United States Patent
O'Connell et al.

(10) Patent No.: US 10,072,236 B2
(45) Date of Patent: *Sep. 11, 2018

(54) DETERGENT COMPOSITION COMPRISING PROTEASE VARIANTS

(71) Applicant: Henkel AG & Co. KGaA, Dusseldorf (DE)

(72) Inventors: Timothy O'Connell, Duesseldorf (DE); Susanne Tondera, Duesseldorf (DE); Hendrik Hellmuth, Duesseldorf (DE); Thomas Weber, Dormagen (DE); Frank Winther Rasmussen, Roskilde (DK); Rolf Thomas Lenhard, Lyngby (DK); Miguel Duarte Guilherme Pereira Toscano, Frederiksberg (DK); Esben Friis, Herlev (DK); Signe Eskildsen Larsen, Kgs. Lyngby (DK); Juergen Carsten Franz Knoetzel, Copenhagen O (DK); Mikael Bauer, Malmo (SE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/907,593

(22) PCT Filed: Jul. 28, 2014

(86) PCT No.: PCT/EP2014/066162
§ 371 (c)(1),
(2) Date: Jan. 26, 2016

(87) PCT Pub. No.: WO2015/024739
PCT Pub. Date: Feb. 26, 2015

(65) Prior Publication Data
US 2016/0160159 A1    Jun. 9, 2016

(30) Foreign Application Priority Data
Jul. 29, 2013    (EP) .................... 13178385

(51) Int. Cl.
*C12N 9/54* (2006.01)
*C11D 3/386* (2006.01)
*C12N 9/50* (2006.01)

(52) U.S. Cl.
CPC .......... *C11D 3/38681* (2013.01); *C11D 3/386* (2013.01); *C12N 9/50* (2013.01); *C12N 9/54* (2013.01); *C12Y 304/21062* (2013.01); *C12Y 304/21* (2013.01)

(58) Field of Classification Search
CPC .... C11P 3/386; C12N 9/54; C12Y 304/21062
See application file for complete search history.

(56) References Cited

U.S. PATENT DOCUMENTS 5,482,849 A    1/1996    Branner et al.
7,294,499 B2 *  11/2007    Svendsen ................. C12N 9/54
                                                 435/216

FOREIGN PATENT DOCUMENTS

WO    2004067737 A2    8/2004
WO    2004083362 A2    9/2004

OTHER PUBLICATIONS

Yoon et al. 2005. Bacillus cibi sp., nov., isolated from jeotgal, a traditonal Korean fermented seafood. International Journal of Systemic and Evolutionary Microbiology. 55: 733-736; sequence alignment attached to reference.*
Neveu et al. 2011; Isolation and characterization of two serine proteases from metagenomics libraries of the Gobi and Death Valley deserts. Applied Microbiology and Biotechnology 91:635-644.*
ISA, European Patent Office, International Search Report and Written Opinion issued in Application No. PCT/EP2014/066162, dated Jun. 16, 2015.

* cited by examiner

*Primary Examiner* — Karen Cochrane Carlson
(74) *Attorney, Agent, or Firm* — Lorenz & Kopf, LLP

(57) ABSTRACT

The present invention relates to detergent compositions comprising protease variants and methods for obtaining such detergent compositions. The present invention also relates to the use of such detergent compositions, especially in laundry or in hard surface cleaning applications.

20 Claims, 1 Drawing Sheet
Specification includes a Sequence Listing.

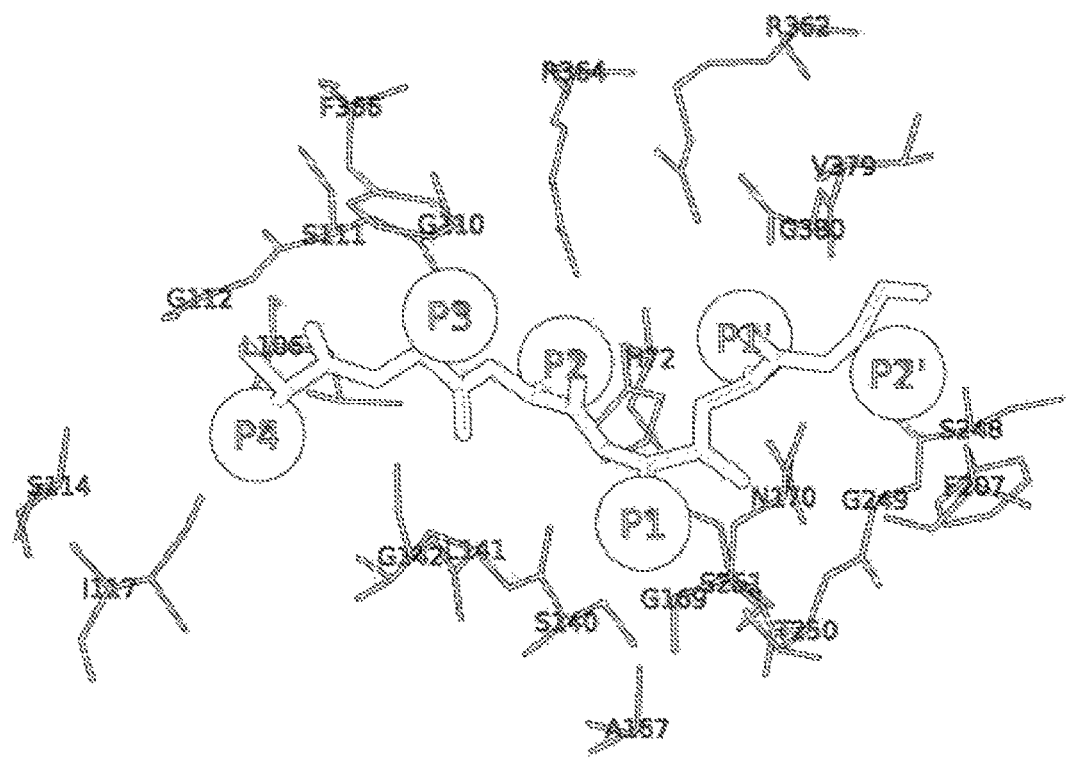

SEQUENCE LISTING

<160> NUMBER OF SEQ ID NOS: 3

<210> SEQ ID NO 1
<211> LENGTH: 1263
<212> TYPE: DNA
<213> ORGANISM: bacillius sp.
<220> FEATURE:
<221> NAME/KEY: CDS
<222> LOCATION: (1)..(1263)
<220> FEATURE:
<221> NAME/KEY: sig_peptide
<222> LOCATION: (1)..(80)
<220> FEATURE:
<221> NAME/KEY: mat_peptide
<222> LOCATION: (331)..(1263)

<400> SEQUENCE: 1

```
atg aag aaa ccg ttg ggg aaa att gtc gca agc acc gca cta ctc         45
Met Lys Lys Pro Leu Gly Lys Ile Val Ala Ser Thr Ala Leu Leu
-110             -105                 -100 att tct gtt gct ttt agt tca tcg atc gca tcg gct gca ctt gca aaa    93
Ile Ser Val Ala Phe Ser Ser Ser Ile Ala Ser Ala Ala Leu Ala Lys
-95                 -90                  -85                 -80 gac aaa gtt gag gta aag gaa caa gat tca tat cgt gtg cta atc aaa   141
Asp Lys Val Glu Val Lys Glu Gln Asp Ser Tyr Arg Val Leu Ile Lys
                -75                  -70                 -65 gca cca act aca tca atc agt act ttt caa tca caa tac gat gtc cgt   189
Ala Pro Thr Thr Ser Ile Ser Thr Phe Gln Ser Gln Tyr Asp Val Arg
            -60                  -55                 -50 tgg gat ttt ggc aaa gag gga ttt aca aca gat gtt gat gcc aaa cag   237
Trp Asp Phe Gly Lys Glu Gly Phe Thr Thr Asp Val Asp Ala Lys Gln
        -45                  -40                 -35 ctc caa acg ctt caa agc aac aaa gac att caa att cag aag gta aat   285
Leu Gln Thr Leu Gln Ser Asn Lys Asp Ile Gln Ile Gln Lys Val Asn
    -30                  -25                 -20 gaa atg aca gta gaa act gtt aca aca gaa aag gcg gaa gtg acg gcg   333
Glu Met Thr Val Glu Thr Val Thr Thr Glu Lys Ala Glu Val Thr Ala
-15                  -10                  -5                 -1  1 gta cca agt aca caa acc cct tgg ggc ata aag tca att tat aat gat   381
Val Pro Ser Thr Gln Thr Pro Trp Gly Ile Lys Ser Ile Tyr Asn Asp
                 5                   10                  15 caa tca att aca aaa aca act gga ggc agc gga att aag gta gct gtt   429
Gln Ser Ile Thr Lys Thr Thr Gly Gly Ser Gly Ile Lys Val Ala Val
             20                  25                  30 tta gat aca ggg gtt tat aca agc cat tta gat tta gct ggt tct gcc   477
Leu Asp Thr Gly Val Tyr Thr Ser His Leu Asp Leu Ala Gly Ser Ala
         35                  40                  45 gag caa tgc aag gat ttt acc caa tct aat cct tta gta gat ggt tca   525
Glu Gln Cys Lys Asp Phe Thr Gln Ser Asn Pro Leu Val Asp Gly Ser
 50                  55                  60                  65 tgc acc gat cgc caa ggg cat ggt aca cat gtt gcc gga act gta ttg   573
Cys Thr Asp Arg Gln Gly His Gly Thr His Val Ala Gly Thr Val Leu
                 70                  75                  80 gcg cat gga ggc agt aat gga caa ggc gtt tac ggg gtg gct ccg caa   621
Ala His Gly Gly Ser Asn Gly Gln Gly Val Tyr Gly Val Ala Pro Gln
             85                  90                  95 gcg aaa cta tgg gca tat aaa gta tta gga gat aac ggc agc gga tac   669
Ala Lys Leu Trp Ala Tyr Lys Val Leu Gly Asp Asn Gly Ser Gly Tyr
        100                 105                 110 tct gat gat att gca gca gct atc aga cat gta gct gat gaa gct tca   717
Ser Asp Asp Ile Ala Ala Ala Ile Arg His Val Ala Asp Glu Ala Ser
    115                 120                 125
```

| | | | |
|---|---|---|---|
| cgt aca ggt tcc aaa gta gta att aat atg tcg cta ggt tca tct gcc | | | 765 |
| Arg Thr Gly Ser Lys Val Val Ile Asn Met Ser Leu Gly Ser Ser Ala | | | |
| 130 135 140 145 | | | |
| | | | |
| aag gat tca ttg att gct agt gca gta gat tat gca tat gga aaa ggt | | | 813 |
| Lys Asp Ser Leu Ile Ala Ser Ala Val Asp Tyr Ala Tyr Gly Lys Gly | | | |
| 150 155 160 | | | |
| | | | |
| gta tta atc gtt gct gcg gct ggt aat agt ggg tca ggc agc aat aca | | | 861 |
| Val Leu Ile Val Ala Ala Ala Gly Asn Ser Gly Ser Gly Ser Asn Thr | | | |
| 165 170 175 | | | |
| | | | |
| atc ggc ttt cct ggc ggg ctt gta aat gca gtg gca gta gcg gca ttg | | | 909 |
| Ile Gly Phe Pro Gly Gly Leu Val Asn Ala Val Ala Val Ala Ala Leu | | | |
| 180 185 190 | | | |
| | | | |
| gag aat gtt cag caa aat gga act tat cga gta gct gat ttc tca tct | | | 957 |
| Glu Asn Val Gln Gln Asn Gly Thr Tyr Arg Val Ala Asp Phe Ser Ser | | | |
| 195 200 205 | | | |
| | | | |
| aga ggg aat ccg gca act gct gga gat tat atc att caa gag cgt gat | | | 1005 |
| Arg Gly Asn Pro Ala Thr Ala Gly Asp Tyr Ile Ile Gln Glu Arg Asp | | | |
| 210 215 220 225 | | | |
| | | | |
| att gaa gtt tca gct ccg gga gca agt gta gag tct aca tgg tac act | | | 1053 |
| Ile Glu Val Ser Ala Pro Gly Ala Ser Val Glu Ser Thr Trp Tyr Thr | | | |
| 230 235 240 | | | |
| | | | |
| ggc ggt tat aat acg atc agc ggt aca tca atg gct aca cct cat gta | | | 1101 |
| Gly Gly Tyr Asn Thr Ile Ser Gly Thr Ser Met Ala Thr Pro His Val | | | |
| 245 250 255 | | | |
| | | | |
| gct ggg tta gct gct aaa atc tgg tca gcg aat act tca tta agt cat | | | 1149 |
| Ala Gly Leu Ala Ala Lys Ile Trp Ser Ala Asn Thr Ser Leu Ser His | | | |
| 260 265 270 | | | |
| | | | |
| agc caa ctg cgc aca gaa ttg caa aat cgc gct aaa gta tat gat att | | | 1197 |
| Ser Gln Leu Arg Thr Glu Leu Gln Asn Arg Ala Lys Val Tyr Asp Ile | | | |
| 275 280 285 | | | |
| | | | |
| aaa ggt ggt atc gga gcc gga aca ggt gac gat tat gca tca ggg ttc | | | 1245 |
| Lys Gly Gly Ile Gly Ala Gly Thr Gly Asp Asp Tyr Ala Ser Gly Phe | | | |
| 290 295 300 305 | | | |
| | | | |
| gga tat cca aga gta aaa | | | 1263 |
| Gly Tyr Pro Arg Val Lys | | | |
| 310 | | | |

```
<210> SEQ ID NO 2
<211> LENGTH: 421
<212> TYPE: PRT
<213> ORGANISM: bacillius sp.

<400> SEQUENCE: 2
```

Met Lys Lys Pro Leu Gly Lys Ile Val Ala Ser Thr Ala Leu Leu
-110                -105                -100

Ile Ser Val Ala Phe Ser Ser Ser Ile Ala Ser Ala Ala Leu Ala Lys
-95             -90              -85                 -80

Asp Lys Val Glu Val Lys Glu Gln Asp Ser Tyr Arg Val Leu Ile Lys
                -75              -70                 -65

Ala Pro Thr Thr Ser Ile Ser Thr Phe Gln Ser Gln Tyr Asp Val Arg
            -60              -55              -50

Trp Asp Phe Gly Lys Glu Gly Phe Thr Thr Asp Val Asp Ala Lys Gln
            -45              -40              -35

Leu Gln Thr Leu Gln Ser Asn Lys Asp Ile Gln Ile Gln Lys Val Asn
    -30              -25              -20

Glu Met Thr Val Glu Thr Val Thr Glu Lys Ala Glu Val Thr Ala
-15              -10              -5              -1  1

Val Pro Ser Thr Gln Thr Pro Trp Gly Ile Lys Ser Ile Tyr Asn Asp
            5                10               15

Gln Ser Ile Thr Lys Thr Thr Gly Gly Ser Gly Ile Lys Val Ala Val
            20                  25                  30

Leu Asp Thr Gly Val Tyr Thr Ser His Leu Asp Leu Ala Gly Ser Ala
        35                  40                  45

Glu Gln Cys Lys Asp Phe Thr Gln Ser Asn Pro Leu Val Asp Gly Ser
 50                  55                  60                  65

Cys Thr Asp Arg Gln Gly His Gly Thr His Val Ala Gly Thr Val Leu
                 70                  75                  80

Ala His Gly Gly Ser Asn Gly Gln Gly Val Tyr Gly Val Ala Pro Gln
                     85                  90                  95

Ala Lys Leu Trp Ala Tyr Lys Val Leu Gly Asp Asn Gly Ser Gly Tyr
            100                 105                 110

Ser Asp Asp Ile Ala Ala Ala Ile Arg His Val Ala Asp Glu Ala Ser
        115                 120                 125

Arg Thr Gly Ser Lys Val Val Ile Asn Met Ser Leu Gly Ser Ser Ala
130                 135                 140                 145

Lys Asp Ser Leu Ile Ala Ser Ala Val Asp Tyr Ala Tyr Gly Lys Gly
                150                 155                 160

Val Leu Ile Val Ala Ala Ala Gly Asn Ser Gly Ser Gly Ser Asn Thr
            165                 170                 175

Ile Gly Phe Pro Gly Gly Leu Val Asn Ala Val Ala Val Ala Ala Leu
        180                 185                 190

Glu Asn Val Gln Gln Asn Gly Thr Tyr Arg Val Ala Asp Phe Ser Ser
        195                 200                 205

Arg Gly Asn Pro Ala Thr Ala Gly Asp Tyr Ile Ile Gln Glu Arg Asp
210                 215                 220                 225

Ile Glu Val Ser Ala Pro Gly Ala Ser Val Glu Ser Thr Trp Tyr Thr
                230                 235                 240

Gly Gly Tyr Asn Thr Ile Ser Gly Thr Ser Met Ala Thr Pro His Val
            245                 250                 255

Ala Gly Leu Ala Ala Lys Ile Trp Ser Ala Asn Thr Ser Leu Ser His
        260                 265                 270

Ser Gln Leu Arg Thr Glu Leu Gln Asn Arg Ala Lys Val Tyr Asp Ile
        275                 280                 285

Lys Gly Gly Ile Gly Ala Gly Thr Gly Asp Asp Tyr Ala Ser Gly Phe
290                 295                 300                 305

Gly Tyr Pro Arg Val Lys
                310

<210> SEQ ID NO 3
<211> LENGTH: 311
<212> TYPE: PRT
<213> ORGANISM: Bacillus sp.

<400> SEQUENCE: 3

Ala Val Pro Ser Thr Gln Thr Pro Trp Gly Ile Lys Ser Ile Tyr Asn
 1               5                  10                  15

Asp Gln Ser Ile Thr Lys Thr Thr Gly Gly Ser Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
 50                  55                  60

Ser Cys Thr Asp Arg Gln Gly His Gly Thr His Val Ala Gly Thr Val

```
65                      70                     75                      80
Leu Ala His Gly Gly Ser Asn Gly Gln Gly Val Tyr Gly Val Ala Pro
            85                      90                      95
Gln Ala Lys Leu Trp Ala Tyr Lys Val Leu Gly Asp Asn Gly Ser Gly
            100                     105                     110
Tyr Ser Asp Asp Ile Ala Ala Ala Ile Arg His Val Ala Asp Glu Ala
            115                     120                     125
Ser Arg Thr Gly Ser Lys Val Val Ile Asn Met Ser Leu Gly Ser Ser
            130                     135                     140
Ala Lys Asp Ser Leu Ile Ala Ser Ala Val Asp Tyr Ala Tyr Gly Lys
145                     150                     155                     160
Gly Val Leu Ile Val Ala Ala Ala Gly Asn Ser Gly Ser Gly Ser Asn
                165                     170                     175
Thr Ile Gly Phe Pro Gly Gly Leu Val Asn Ala Val Ala Val Ala Ala
                180                     185                     190
Leu Glu Asn Val Gln Gln Asn Gly Thr Tyr Arg Val Ala Asp Phe Ser
                195                     200                     205
Ser Arg Gly Asn Pro Ala Thr Ala Gly Asp Tyr Ile Ile Gln Glu Arg
        210                     215                     220
Asp Ile Glu Val Ser Ala Pro Gly Ala Ser Val Glu Ser Thr Trp Tyr
225                     230                     235                     240
Thr Gly Gly Tyr Asn Thr Ile Ser Gly Thr Ser Met Ala Thr Pro His
                245                     250                     255
Val Ala Gly Leu Ala Ala Lys Ile Trp Ser Ala Asn Thr Ser Leu Ser
                260                     265                     270
His Ser Gln Leu Arg Thr Glu Leu Gln Asn Arg Ala Lys Val Tyr Asp
        275                     280                     285
Ile Lys Gly Gly Ile Gly Ala Gly Thr Gly Asp Asp Tyr Ala Ser Gly
        290                     295                     300
Phe Gly Tyr Pro Arg Val Lys
305                     310
```

DETERGENT COMPOSITION COMPRISING PROTEASE VARIANTS

CROSS-REFERENCE TO RELATED APPLICATION

This application is a U.S. National-Stage entry under 35 U.S.C. § 371 based on International Application No. PCT/EP2014/066162, filed Jul. 28, 2014, which was published under PCT Article 21(2) and which claims priority to European Application No. 13178385.4, filed Jul. 29, 2013, which are all hereby incorporated in their entirety by reference.

REFERENCE TO A SEQUENCE LISTING

This application contains a Sequence Listing in computer readable form, which is incorporated herein by reference.

BACKGROUND

Embodiments herein relate to a detergent composition comprising novel protease variants exhibiting alterations relative to the parent protease in one or more properties including: wash performance, detergent stability and/or storage stability. Further, embodiments herein relate to methods of producing said detergent compositions and to the use of said detergent compositions in cleaning applications. In addition, other objects, desirable features and characteristics will become apparent from the subsequent summary and detailed description, and the appended claims, taken in conjunction with the accompanying drawings and this background.

DESCRIPTION OF THE RELATED ART

Enzymes have been used within the detergent industry as part of washing formulations for many decades. Proteases are from a commercial perspective the most relevant enzyme in such formulations, but other enzymes including lipases, amylases, cellulases, hemicellulases or mixtures of enzymes are also often used. To improve the cost and/or the performance of proteases there is an ongoing search for proteases with altered properties, such as increased activity at low temperatures, increased stability, increased specific activity at a given pH, altered Ca2+ dependency, increased stability in the presence of other detergent ingredients (e.g., bleach, surfactants etc.) etc. One family of proteases, which are often used in detergents, are the subtilases. This family has previously been further grouped into 6 different sub-groups by Siezen R J and Leunissen J A M, 1997, Protein Science, 6, 501-523. One of these sub-groups is the Subtilisin family which includes subtilases such as BPN', subtilisin 309 (SAVINASE®, Novozymes A/S), subtilisin Carlsberg (AL-CALASE®, Novozymes A/S), subtilisin S41 (a subtilase from the psychrophilic Antarctic Bacillus TA41, Davail S et al. 1994, The Journal of Biological Chemistry, 269(26), 99. 17448-17453) and subtilisin S39 (a subtilase from the psychrophilic Antarctic Bacillus TA39, Narinx E et al. 1997, Protein Engineering, 10 (11), pp. 1271-1279). TY-145 is a subtilase from Bacillus sp. TY-145, NCIMB 40339, which was first described in WO 92/17577 (Novozymes A/S) and in the later application WO2004/067737 (Novozymes A/S) disclosing the three-dimensional structure and the use of protein engineering to alter functionality of a TY-145 subtilase.

SUMMARY

According to an exemplary embodiment, a detergent composition is provided and includes a protease variant. The protease variant comprises a substitution of at least one amino acid in the loop corresponding to positions 171, 173, 175 or 179 of SEQ ID NO: 3. Also, the protease variant has a sequence identity to SEQ ID NO: 3 of at least 70% and less than 100%. Further, the protease variant has protease activity.

In accordance with another embodiment, a method for using a detergent composition in a cleaning process is provided. The detergent composition comprises a protease variant having a substitution of at least one amino acid in the loop corresponding to positions 171, 173, 175 or 179 of SEQ ID NO: 3. Further, the protease variant has a sequence identity to SEQ ID NO: 3 of at least 70% and less than 100%. Also, the protease variant has protease activity.

In yet another embodiment, a method for producing a detergent composition is provided. The method includes obtaining a protein variant by introducing into a parent protease a substitution at one or more positions corresponding to positions 171, 173, 175 or 179 of SEQ ID NO: 3, and recovering the protease variant, wherein the protease variant has an amino acid sequence which is at least 70% identical to SEQ ID NO: 3. The method further includes adding the protease variant to the detergent composition.

BRIEF DESCRIPTION OF THE DRAWING

Detergent compositions and methods for producing detergent compositions will hereinafter be described in conjunction with the following drawing figure, wherein like numerals denote like elements, and wherein:

The FIGURE is a schematic depicting a portion of the structure of a protease.

OVERVIEW OF SEQUENCES LISTING

SEQ ID NO 1=is the DNA sequence of TY-145 protease isolated from Bacillus sp.
SEQ ID NO 2=is the amino acid sequence as deduced from SEQ ID NO: 1.
SEQ ID NO 3=is the amino acid sequence of the mature TY-145.

Definitions

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The term "subtilases" refer to a sub-group of serine protease according to Siezen et al., Protein Engng. 4 (1991) 719-737 and Siezen et al. Protein Science 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Exemplary proteases herein are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes herein, protease activity is determined according to the procedure described in "Materials and Methods" below. Exemplary protease variants herein have at least 20%, e.g., at least 40%, at least 50%, at least 60%, at least 70%, at least 80%, at least 90%, at least 95%, or at least 100% of the protease activity of the mature polypeptide with SEQ ID NO: 3.

The term "parent" or "protease parent" means a protease to which an alteration is made to produce the enzyme variants described herein. Thus the parent is a protease having the identical amino acid sequence of said variant but not having the alterations at one or more of said specified positions. It will be understood, that in the present context the expression "having identical amino acid sequence" relates to 100% sequence identity. The parent may be a naturally occurring (wild-type) polypeptide or a variant thereof. In a particular embodiment the parent is a protease with at least 70%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, e.g., at least 99.1%, at least 99.2%, at least 99.3%, at least 99.4%, at least 99.5%, at least 99.6%, or 100% identity to a polypeptide with SEQ ID NO: 3.

The term "protease variant" means a protease having protease activity comprising an alteration, i.e., a substitution, insertion, and/or deletion, (in an exemplary embodiment a substitution), at one or more (or one or several) positions compared to its parent which is a protease having the identical amino acid sequence of said variant but not having the alterations at one or more of said specified positions. A substitution means a replacement of an amino acid occupying a position with a different amino acid; a deletion means removal of an amino acid occupying a position; and an insertion means adding amino acids e.g., 1 to 10 amino acids, such as 1 to 3 amino acids adjacent to an amino acid occupying a position.

The term "isolated variant" means a variant that is modified by the hand of man. In one aspect, the variant is at least about 1% pure, e.g., at least about 5% pure, at least about 10% pure, at least about 20% pure, at least about 40% pure, at least about 60% pure, at least about 80% pure, and at least about 90% pure, as determined by SDS-PAGE.

The term "isolated polynucleotide" means a polynucleotide that is modified by the hand of man. In one aspect, the isolated polynucleotide is at least about 1% pure, e.g., at least about 5% pure, at least about 10% pure, at least about 20% pure, at least about 40% pure, at least about 60% pure, at least about 80% pure, at least about 90% pure, and at least about 95% pure, as determined by agarose electrophoresis. The polynucleotides may be of genomic, cDNA, RNA, semisynthetic, synthetic origin, or any combinations thereof.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "substantially pure variant" means a preparation that contains at most about 10%, at most about 8%, at most about 6%, at most about 5%, at most about 4%, at most about 3%, at most about 2%, at most about 1%, and at most about 0.5% by weight of other polypeptide material with which it is natively or recombinantly associated. In an exemplary embodiment, the variant is at least about 92% pure, e.g., at least about 94% pure, at least about 95% pure, at least about 96% pure, at least about 97% pure, at least about 98% pure, at least about 99%, at least about 99.5% pure, or about 100% pure, by weight of the total polypeptide material present in the preparation. The variants in exemplary detergent compositions herein are in a substantially pure form. This can be accomplished, for example, by preparing the variant by well known recombinant methods or by classical purification methods.

The term "wild-type protease" means a protease expressed by a naturally occurring organism, such as a bacterium, archaea, yeast, fungus, plant or animal found in nature. An example of a wild-type protease is TY-145 i.e. the mature polypeptide of SEQ ID NO 2 i.e. amino acids 1 to 311 or the mature polypeptide with SEQ ID NO 3.

The term "mature polypeptide" means a polypeptide in its final form following translation and any post-translational modifications, such as N-terminal processing, C-terminal truncation, glycosylation, phosphorylation, etc. In one aspect, the mature polypeptide corresponds to the amino acid sequence with SEQ ID NO: 3.

The term "mature polypeptide coding sequence" means a polynucleotide that encodes a mature polypeptide having protease activity. In one aspect, the mature polypeptide coding sequence is nucleotides 331 to 1263 of SEQ ID NO: 1 based on the SignalP (Nielsen et al., 1997, Protein Engineering 10: 1-6)] that predicts nucleotides 1 to 81 of SEQ ID NO: 1 is the signal peptide.

The term "cDNA" means a DNA molecule that can be prepared by reverse transcription from a mature, spliced, mRNA molecule obtained from a prokaryotic or eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The relatedness between two amino acid sequences or between two nucleotide sequences is described by the parameter "sequence identity". For purposes herein, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "improved property" means a characteristic associated with a variant that is improved compared to the parent or compared to a protease with SEQ ID NO: 3, or compared to a protease having the identical amino acid sequence of said variant but not having the alterations at one or more of said specified positions. Such improved properties include, but are not limited to, wash performance, protease activity, thermal activity profile, thermostability, pH activity profile, pH stability, substrate/cofactor specificity, improved surface properties, substrate specificity, product specificity, increased stability, improved stability under storage conditions, and chemical stability.

The term "improved protease activity" is defined herein as an altered protease activity (as defined above) of a protease variant displaying an alteration of the activity relative (or compared) to the activity of the parent protease, or compared to a protease with SEQ ID NO: 3, or relative to a protease having the identical amino acid sequence of said variant but not having the alterations at one or more of said specified positions, by increased protein conversion.

The term "stability" includes storage stability and stability during use, e.g., during a wash process and reflects the stability of the protease variant in the detergent composition described herein as a function of time, e.g., how much activity is retained when the protease variant is kept in solution in particular in a detergent solution. The stability is influenced by many factors, e.g., pH, temperature, detergent composition, e.g., amount of builder, surfactants, etc. The protease stability may be measured using the assay described in example 2. The term "improved stability" or "increased stability" is defined herein as a variant protease displaying an increased stability in solutions, relative to the stability of the parent protease, relative to a protease having the identical amino acid sequence of said variant but not having the alterations at one or more of said specified positions or relative to SEQ ID NO: 3. The terms "improved stability" and "increased stability" includes "improved chemical stability", "detergent stability" or "improved detergent stability".

The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants being more able to catalyze a reaction in the presence of such chemicals. In a particular aspect of an embodiment herein, the improved chemical stability is an improved stability in a detergent, in particular in a liquid detergent. The term "detergent stability" or "improved detergent stability is in particular an improved stability of the protease activity when a protease variant described herein is mixed into a liquid detergent formulation, especially into a liquid detergent formulation according to table 1, and then stored at temperatures of from about 15 to about 50° C., e.g., about 20° C., about 30° C. or about 40° C. In an exemplary embodiment, liquid detergents are particular useful as liquid laundry detergents or liquid dish washing compositions.

The term "improved thermal activity" means a variant displaying an altered temperature-dependent activity profile at a specific temperature relative to the temperature-dependent activity profile of the parent or relative to a protease with SEQ ID NO: 3. The thermal activity value provides a measure of the variant's efficiency in enhancing catalysis of a hydrolysis reaction over a range of temperatures. A more thermoactive variant will lead to an increase in enhancing the rate of hydrolysis of a substrate by an enzyme composition thereby decreasing the time required and/or decreasing the enzyme concentration required for activity. Alternatively, a variant with a reduced thermal activity will enhance an enzymatic reaction at a temperature lower than the temperature optimum of the parent defined by the temperature-dependent activity profile of the parent.

The term "improved wash performance" is defined herein as a detergent composition comprising a protease variant described herein wherein the protease variant displays an improved wash performance relative to the wash performance of the parent protease, relative to a protease with SEQ ID NO: 3 or relative to a protease having the identical amino acid sequence of said variant but not having the alterations at one or more of said specified positions, e.g., by increased stain removal. The term "wash performance" includes wash performance in laundry but also, for example, in dish wash. The wash performance may be quantified as described under the definition of "wash performance" herein.

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended embodiments herein be limited to any particular detergent formulation or composition.

The term "detergent composition" is not intended to be limited to compositions that contain surfactants. It is intended that in addition to the variants in the detergent composition described herein, the term encompasses detergents that may contain, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "fabric" encompasses any textile material. Thus, it is intended that the term encompass garments, as well as fabrics, yarns, fibers, non-woven materials, natural materials, synthetic materials, and any other textile material.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "non-fabric detergent compositions" include non-textile surface detergent compositions, including but not limited to compositions for hard surface cleaning, such as dishwashing detergent compositions, oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a protease variant refers to the quantity of protease variant described hereinbefore that achieves a desired level of enzymatic activity, e.g., in a defined detergent composition.

The term "water hardness" or "degree of hardness" or "dH" or "° dH" as used herein refers to German degrees of hardness. One degree is defined as 10 milligrams of calcium oxide per liter of water.

The term "relevant washing conditions" is used herein to indicate the conditions, particularly washing temperature, time, washing mechanics, detergent concentration, type of detergent and water hardness, actually used in households in a detergent market segment.

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the protease variant enzyme used in the composition. In some embodiments, granular compositions are in "compact" form, while in other embodiments, the liquid compositions are in a "concentrated" form.

The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (fats and oils), pectinase on pectin and hemicellulases on hemicellulose. Stains are often depositions of complex mixtures of different components which either results in a local discolouration of the material by itself or which leaves a sticky surface on the object which may attract soils dissolved in the washing liquor thereby resulting in discolouration of the stained area. When an enzyme acts on its specific substrate present in a stain the enzyme degrades or partially degrades its substrate thereby aiding the removal of soils and stain components associated with the substrate during the washing process. For example, when a protease acts on a grass stain it degrades the protein components in the grass and allows the green/brown colour to be released during washing.

The term "reduced amount" means in this context that the amount of the component is smaller than the amount which would be used in a reference process under otherwise the same conditions. In an exemplary embodiment the amount is reduced by, e.g., at least 5%, such as at least 10%, at least 15%, at least 20% or as otherwise herein described.

The term "low detergent concentration" system includes detergents where less than about 800 ppm of detergent components is present in the wash water. Asian, e.g., Japanese detergents are typically considered low detergent concentration systems.

The term "medium detergent concentration" system includes detergents wherein from about 800 ppm to about 2000 ppm of detergent components is present in the wash water. North American detergents are generally considered to be medium detergent concentration systems.

The term "high detergent concentration" system includes detergents wherein greater than about 2000 ppm of detergent components is present in the wash water. European detergents are generally considered to be high detergent concentration systems.

Conventions for Designation of Variants

For purposes herein, the mature polypeptide disclosed in SEQ ID NO: 3 is used to determine the corresponding amino acid residue in another protease. The amino acid sequence of another protease is aligned with the mature polypeptide disclosed in SEQ ID NO: 3, and based on the alignment, the amino acid position number corresponding to any amino acid residue in the mature polypeptide disclosed in SEQ ID NO: 3 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another protease can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680), using their respective default parameters.

When the other enzyme has diverged from the mature polypeptide of SEQ ID NO: 3 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP super families of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants herein, the nomenclature described below is adapted for ease of reference. The accepted IUPAC single letter or three letters amino acid abbreviations are employed. Amino acid positions are indicated with $\#_1$, $\#_2$, etc.

Substitutions: For an amino acid substitution, the following nomenclature is used: Original amino acid, position, substituted amino acid. Accordingly, the substitution of serine at position #1 with tryptophan is designated as "Ser#1Trp" or "S#1W". Multiple mutations are separated by addition marks ("+") or by commas (,), e.g., "Ser#1Trp+Ser#2Pro" or S#1W, S#2P, representing substitutions at positions #1 and #2 of serine (S) with tryptophan (W) and proline (P), respectively. If more than one amino acid may be substituted in a given position these are listed in brackets, such as [X] or {X}. Thus if both Trp and Lys according to embodiments herein may be substituted instead of the amino acid occupying at position #1 this is indicated as X#1 {W, K} or X#2 [W, K] where the X indicate that different proteases may be parent, e.g., such as a protease with SEQ ID NO 3 or a protease having at least 70% identity hereto. Thus in some cases the variants are represented as #1 {W, K} or X#2P indicating that the amino acids to be substituted vary depending on the parent.

Deletions: For an amino acid deletion, the following nomenclature is used: Original amino acid, position, *. Accordingly, the deletion of serine at position #1 is designated as "Ser#1*" or "S#1*". Multiple deletions are separated by addition marks ("+") or commas, e.g., "Ser#1*+Ser#2*" or "S#1*, S#2*".

Insertions: The insertion of an additional amino acid residue such as, for example, a lysine after G#1 may be indicated by: Gly#1GlyLys or G#1GK. Alternatively insertion of an additional amino acid residue such as lysine after G#1 may be indicated by: *#1aL. When more than one amino acid residue is inserted, such as, for example, a Lys, and Ala after #1 this may be indicated as: Gly#1GlyLysAla or G#1GKA. In such cases, the inserted amino acid residue(s) may also be numbered by the addition of lower case letters to the position number of the amino acid residue preceding the inserted amino acid residue(s), in this example: *#1aK*#1bA.

Multiple alterations. Variants comprising multiple alterations are separated by addition marks ("+") or by commas (,), e.g., "Ser#1Trp+Ser#2Pro" or "S#1W, S#2P" representing a substitution of serine at positions #1 and #2 with tryptophan and proline, respectively as described above.

Different alterations. Where different alterations can be introduced at a position, the different alterations are separated by a comma, e.g., "Ser#1Trp, Lys" or S#1W, K represents a substitution of serine at position #1 with tryptophan or lysine. Thus, "Ser#1Trp, Lys+Ser#2Asp" designates the following variants: "Ser$\#_1$Trp+Ser$\#_2$Pro", "Ser$\#_1$Lys+Ser$\#_2$Pro" or S$\#_1$W, K+S$\#_2$D.

DETAILED DESCRIPTION

The following detailed description is merely exemplary in nature and is not intended to limit the detergent composition or the application and uses of the detergent composition.

Furthermore, there is no intention to be bound by any theory presented in the preceding background or the following detailed description.

An exemplary embodiment of a detergent composition described herein concerns protease variants, comprising a substitution of one or more amino acids in the loop corresponding to positions 171, 173, 175 or 179 of SEQ ID NO: 3, wherein the variant has a sequence identity to SEQ ID NO: 3 of at least 70% and less than 100%, and wherein the variant has protease activity.

Previously unanticipated, the inventors have found that protease variants containing one or more substitutions corresponding to the positions 171, 173, 175 or 179 of SEQ ID NO 3 have improved stability in detergent compared to a protease having the identical amino acid sequence of said variant but not having the substitution(s) at one or more of said specified positions or compared to a protease with SEQ ID NO: 3. The amino acids corresponding to positions 171, 173, 175 or 179 of SEQ ID NO: 3 form part of an active site loop corresponding to positions 170 to 180 of SEQ ID NO: 3, which defines parts of the S1 substrate binding pocket, see the FIGURE. Thus the exemplary detergent composition provides protease variants, comprising a substitution at one or more (e.g., several) positions corresponding to positions 171, 173, 175 and 179, wherein the variant has protease activity. New protease variants containing one or more substitution(s) in the loop region 170-180 (SEQ ID NO: 3 numbering), were generated and tested for stability in detergent as described in "Material and Methods" and the inventors demonstrate that one or more substitutions of one or more amino acid at a position corresponding to positions 171, 173, 175 and 179 of the mature polypeptide SEQ ID NO: 3 significantly improved the detergent stability compared to a protease having the identical amino acid sequence of said variant but not having a substitution at one or more of said specified positions or compared to a protease with SEQ ID NO: 3. Whenever the terms "variant(s)" or "protease variant(s)" are mentioned further on, they refer to detergent compositions comprising such protease variant(s).

Surprisingly the variants in an exemplary detergent composition described herein may, in addition to improved stability, also have improved wash performance. Thus, in an exemplary embodiment, the variants in the detergent composition described herein have improved detergent stability and/or improved wash performance compared to a protease having the identical amino acid sequence of said variant but not having a substitution at one or more of said specified positions, or compared to a protease with SEQ ID NO: 3. In an exemplary embodiment, the protease variant comprises a substitution of one or more amino acids in the loop corresponding to positions 171, 173, 175 or 179 of SEQ ID NO: 3, wherein the variant has at least 70% identity to the protease with SEQ ID NO: 3 (*Bacillus* sp. TY-145). Thus, one aspect of an exemplary embodiment relates to detergent composition comprising a protease variant, the variant comprises a substitution at one or more positions corresponding to positions 171, 173, 175 or 179 of SEQ ID NO: 3, wherein the variant has an amino acid sequence which is at least 70% identical to SEQ ID NO: 3; and recovering the variant. Thus, an embodiment relates to such detergent compositions comprising a protease variant wherein the variant comprises substitution of one or more amino acids in the loop corresponding to positions 171, 173, 175 or 179, of SEQ ID NO: 3, wherein the variant has at least 70% such as at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100%, sequence identity to SEQ ID NO: 3. In one embodiment, the variant is a polypeptide encoded by a polynucleotide having at least 70% identity to the mature polypeptide coding sequence of SEQ ID NO: 1, or a sequence encoding the mature polypeptide of SEQ ID NO: 2. In one embodiment, the variant in the detergent composition described herein is a polypeptide encoded by a polynucleotide having at least 70% identity, e.g., at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100%, sequence identity to the mature polynucleotide of SEQ ID NO: 1.

A particular embodiment concerns a detergent composition comprising a protease variant, wherein the variant comprises a substitution at one or more positions corresponding to positions 171, 173, 175 or 179 of SEQ ID NO: 3, wherein the variant is a variant of a parent protease which has at least 70%, such as at least 75%, e.g., such as at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, e.g., at least 99.1%, at least 99.2%, at least 99.3%, at least 99.4%, at least 99.5%, at least 99.6%, or 100% sequence identity to SEQ ID NO: 3. In one particular embodiment the protease variant is a TY-145 (SEQ ID NO: 3) variant comprising a substitution of one or more amino acids in the loop corresponding to positions 171, 173, 175 or 179 of SEQ ID NO: 3. Another embodiment relates to a variant comprising a substitution at two, three, four or five positions corresponding to positions 171, 173, 175, 179, and 180 of SEQ ID NO: 3. An exemplary embodiment concerns a protease variant, comprising substitution of one or more amino acids in the loop corresponding to positions 171, 173, 175 or 179 of SEQ ID NO: 3, wherein the variant has at least 70%, such as at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100%, sequence identity to SEQ ID NO: 3. An exemplary embodiment concerns a detergent composition comprising a protease variant wherein the protease variant comprises a substitution of one or more amino acid selected from the group consisting of Cys, Val, Gln, Thr, Glu, His, Lys, Met, Asn, Tyr, Ale, Pro and Trp in the loop corresponding to positions 171, 173, 175 or 179 of SEQ ID NO: 3. A particular embodiment concerns a protease variant comprising a substitution of one or more amino acid selected from the group consisting of Cys, Val, Gln, Thr, Glu, His, Lys, Met, Asn, Tyr, Ale, Pro and Trp in the loop corresponding to positions 171, 173, 175 or 179 of SEQ ID NO: 3, wherein the variant has at least 70% identity to SEQ ID NO: 3 such as at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100%, sequence identity to SEQ ID NO: 3. Another particular embodiment concerns a detergent composition comprising a protease variant wherein the protease variant comprises one or more of the substitutions selected from the group consisting of S171{W, K, E}; S173P; S175 {A, V, P} or G179{C, V, Q, S, T, E, H, K, M, N} of SEQ ID NO: 3, wherein the variant has at least 70% identity to SEQ ID NO: 3 such as at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100%, sequence identity to the SEQ ID NO: 3.

In one aspect, the detergent composition comprises a protease variant wherein the protease variant comprises a substitution at position 171, in an exemplary aspect the variant comprises a substitution at position 171 with W, K or E, in another exemplary aspect, the variant comprises an W at position 171, in yet another exemplary aspect, the variant comprises the substitution S171W, wherein the parent is the mature polypeptide with SEQ ID NO: 3. In another exemplary aspect, the variant comprises an K at position 171, in yet another exemplary aspect, the variant comprises the substitution S171K, wherein the parent is the mature polypeptide with SEQ ID NO: 3. in another exemplary aspect, the variant comprises an E at position 171, in yet another exemplary aspect, the variant comprises the substitution S171E, wherein the parent is the mature polypeptide with SEQ ID NO: 3.

In a further aspect, the detergent composition comprises a protease variant wherein the variant comprises a substitution at position 171 with W, K or E wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another exemplary aspect, the variant comprises an W at position 171, in yet another exemplary aspect, the variant comprises the substitution S171W, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another exemplary aspect, the variant comprises an K at position 171, in yet another exemplary aspect, the variant comprises the substitution S171K, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another exemplary aspect, the variant comprises an E at position 171, in yet another exemplary aspect, the variant comprises the substitution S171E, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In an even further aspect, the detergent composition comprises a protease variant wherein the variant comprises a substitution at position 171 with W, K or E wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in Example 2 as described under "Material and Methods". In another aspect, the variant comprises a W at position 171, in yet another aspect, the variant comprises the substitution S171W, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100%, and having an increased stability relative to a protease with SEQ ID NO: 3 or a protease parent having the identical amino acid sequence of said variant but not having the substitutions at one or more of said positions, when tested in the Example 2 as described under "Material and Methods". In another aspect, the detergent composition comprises a protease variant wherein the variant comprises an K at position 171, in yet another aspect, the variant comprises the substitution S171K, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods". In another aspect, the variant comprises an E at position 171, in yet another aspect, the variant comprises the substitution S171E, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods"

In one aspect, the detergent composition comprises a protease variant wherein the protease variant comprises a substitution at position 173, in an aspect the variant comprises a substitution at position 173 with P; in another aspect, the variant comprises the substitution S173P, wherein the parent is polypeptide with SEQ ID NO: 3. In another aspect, the variant comprises an P at position 173, in yet another aspect, the variant comprises the substitution S173P, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In a further aspect, the variant comprises a substitution at position 173 with P, in yet another aspect, the variant comprises the substitution S173P, wherein the variant has at least 70% sequence identity to SEQ ID NO: 2, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 2, and having an increased stability relative to a protease with SEQ ID NO: 3 or a protease parent having the identical amino acid sequence of said variant but not having the substitutions at one or more of said positions, when tested in Example 2 as described under "Material and Methods".

In one aspect, the detergent composition comprises a protease variant wherein the protease variant comprises a substitution at position 175, in an aspect the variant comprises a substitution at position 175 with A, V or P, in another aspect, the variant comprises an A at position 175, in yet another aspect, the variant comprises the substitution S175A, wherein the parent is a polypeptide with SEQ ID NO: 3. In another aspect, the variant comprises an V at position 175, in yet another aspect, the variant comprises the substitution S175V, wherein the parent is the mature polypeptide with SEQ ID NO: 3. In another aspect, the variant comprises an P at position 175, in yet another aspect, the variant comprises the substitution S175P, wherein the parent is a polypeptide with SEQ ID NO: 3.

In a further aspect, the detergent composition comprises a protease variant wherein the variant comprises a substitution at position 175 with A, V or P wherein the variant has at least 70% sequence identity to SEQ ID NO: 3, such as at least 75%, at least 80%, at least 85%, at least 90%, at least 95%, at least 96%, at least 97%, at least 98%, or at least 99%, but less than 100% sequence identity to SEQ ID NO: 3. In another aspect, the variant comprises an A at position 175, in yet another aspect, the variant comprises the substitution S175A, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises an V at position 175, in yet another aspect, the variant comprises the substitution S175V, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises an P at position 175, in yet another aspect, the variant comprises the substitution S175P, wherein the variant has at least 70% sequence identity to SEQ ID NO: 3, such at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In a aspect, the variant comprises a substitution at position 175 with A, V or P wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in Example 2 as described under "Material and Methods". In another aspect, the detergent composition comprises a protease variant wherein the variant comprises an A at position 175, in yet another aspect, the variant comprises the substitution S175A, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods". In another aspect, the variant comprises an V at position 175, in yet another aspect, the variant comprises the substitution S175V, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods". In another aspect, the variant comprises an P at position 175, in yet another aspect, the variant comprises the substitution S175P, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises a C at position 179, in yet another aspect, the variant comprises the substitution G179C, wherein the parent is a polypeptide with SEQ ID NO: 3. In a further aspect, the variant comprises a substitution at position 179 with C, in yet another aspect, the variant comprises the substitution G179C, wherein the variant has at least 70% sequence identity to SEQ ID NO: 2, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 2. In another aspect, the variant comprises a substitution at position 179 with C, in yet another aspect, the variant comprises the substitution G179C, wherein the variant has at least 70% sequence identity to SEQ ID NO: 2, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 2, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises a V at position 179, in yet another aspect, the variant comprises the substitution G179V, wherein the parent is a polypeptide with SEQ ID NO: 3. In a further aspect, the variant comprises a substitution at position 179 with V, in yet another aspect, the variant comprises the substitution G179V, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with V, in yet another aspect, the variant comprises the substitution G179V, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises a Q at position 179, in yet another aspect, the variant comprises the substitution G179Q, wherein the parent is a polypeptide with SEQ ID NO: 3. In a further aspect, the variant comprises a substitution at position 179 with Q, in yet another aspect, the variant comprises the substitution G179Q, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with Q, in yet another aspect, the variant comprises the substitution G179Q, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises an S at position 179, in yet another aspect, the variant comprises the substitution G179S, wherein the parent is a polypeptide with SEQ ID NO: 3. In a further aspect, the variant comprises a substitution at position 179 with S, in yet another aspect, the variant comprises the substitution G179, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with S, in yet another aspect, the variant comprises the substitution G179, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises an T at position 179, in yet another aspect, the variant comprises the substitution G179T, wherein the parent is a polypeptide with SEQ ID NO: 3. In a further aspect, the variant comprises a substitution at position 179 with T, in yet another aspect, the variant comprises the substitution G179T, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with T, in yet another aspect, the variant comprises the substitution G179T, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100%, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the variant detergent composition comprises a protease variant wherein the comprises an E at position 179, in yet another aspect, the variant comprises the substitution G179E, wherein the parent is a polypeptide with SEQ ID NO: 3. In a further aspect, the variant comprises a substitution at position 179 with E, in yet another aspect, the variant comprises the substitution G179E, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with E, in yet another aspect, the variant comprises the substitution G179E, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises an H at position 179, in yet another aspect, the variant comprises the substitution G179H, wherein the parent is a polypeptide with SEQ ID NO: 3. In a further aspect, the variant comprises a substitution at position 179 with H, in yet another aspect, the variant comprises the substitution G179H, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with H, in yet another aspect, the variant comprises the substitution G179H, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods" In another aspect, the detergent composition comprises a protease variant wherein the variant comprises a K at position 179, in yet another aspect, the variant comprises the substitution G179K, wherein the parent is a polypeptide with SEQ ID NO: 3. In a further aspect, the variant comprises a substitution at position 179 with K, in yet another aspect, the variant comprises the substitution G179K, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with K, in yet another aspect, the variant comprises the substitution G179K, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises an M at position 179, in yet another aspect, the variant comprises the substitution G179M, wherein the parent is a polypeptide with SEQ ID NO: 3. In a further aspect, the variant comprises a substitution at position 179 with M, in yet another aspect, the variant comprises the substitution G179M, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises a substitution at position 179 with M, in yet another aspect, the variant comprises the substitution G179M, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

In another aspect, the detergent composition comprises a protease variant wherein the variant comprises an N at position 179, in yet another aspect, the variant comprises the substitution G179N, wherein the parent is a polypeptide with SEQ ID NO: 3. In a further aspect, the detergent composition comprises a protease variant wherein the variant comprises a substitution at position 179 with N, in yet another aspect, the variant comprises the substitution G179N, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In a further aspect, the variant comprises a substitution at position 179 with N, in yet another aspect, the variant comprises the substitution G179N, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in the Example 2 as described under "Material and Methods".

One aspect, the detergent composition comprises a protease variant wherein the protease variant further comprises a substitution at position 180, in an aspect the variant further comprises a substitution at position 180 with Y. In another aspect, the variant further comprises the substitution F180Y, wherein the parent is a polypeptide with SEQ ID NO: 3. In a further aspect, the variant comprises a substitution at position 180 with Y, in yet another aspect, the variant further comprises the substitution F180Y, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3. In another aspect, the variant comprises an Y at position 180, in yet another aspect, the variant comprises the substitution F180Y, wherein the variant has at least 70% sequence identity to SEQ ID NO: 3, such as at least 75%, at least 80%, at least 85%, at least 90%, at least 95%, at least 96%, at least 97%, at least 98%, or at least 99%, e.g., at least 99.1%, at least 99.2%, at least 99.3%, at least 99.4%, at least 99.5%, or at least 99.6%, but less than 100% sequence identity to SEQ ID NO: 3, and having an increased stability relative to a protease with SEQ ID NO: 3 or a protease parent having the identical amino acid sequence of said variant but not having the substitutions at one or more of said positions, when tested in Example 2 as described under "Material and Methods".

In another aspect, the detergent composition comprises a protease variant wherein the variant comprises substitutions at positions corresponding to positions 171 and 173, such as those described above.

In another aspect, the variant comprises substitutions at positions corresponding to positions 171 and 175, such as those described above.

In another aspect, the variant comprises substitutions at positions corresponding to positions 171 and 179, such as those described above.

In another aspect, the variant comprises substitutions at positions corresponding to positions 171 and 180, such as those described above.

In another aspect, the variant comprises substitutions at positions corresponding to positions 173 and 175, such as those described above.

In another aspect, the variant comprises substitutions at positions corresponding to positions 173 and 179, such as those described above.

In another aspect, the variant comprises substitutions at positions corresponding to positions 173 and 180, such as those described above.

In another aspect, the variant comprises substitutions at positions corresponding to positions 175 and 179, such as those described above.

In another aspect, the variant comprises substitutions at positions corresponding to positions 175 and 180, such as those described above.

In another aspect, the variant comprises substitutions at positions corresponding to positions 171, 173, and 175, such as those described above.

In another aspect, the variant comprises substitutions at positions corresponding to positions 171, 173, and 179, such as those described above.

In another aspect, the variant comprises substitutions at positions corresponding to positions 171, 173, and 180, such as those described above.

In another aspect, the variant comprises substitutions at positions corresponding to positions 171, 175, and 179, such as those described above.

In another aspect, the variant comprises substitutions at positions corresponding to positions 171, 175, and 180, such as those described above.

In another aspect, the variant comprises substitutions at positions corresponding to positions 171, 179, and 180, such as those described above.

In another aspect, the variant comprises substitutions at positions corresponding to positions 173, 175, and 179, such as those described above.

In another aspect, the variant comprises substitutions at positions corresponding to positions 173, 175, and 180, such as those described above.

In another aspect, the variant comprises substitutions at positions corresponding to positions 175, 179, and 180, such as those described above.

In another aspect, the variant comprises substitutions at positions corresponding to positions 171, 173, 175, and 179, such as those described above.

In another aspect, the variant comprises substitutions at positions corresponding to positions 171, 173, 175, and 180, such as those described above.

In another aspect, the variant comprises substitutions at positions corresponding to positions 173, 175, 179 and 180, such as those described above.

In another aspect, the variant comprises substitutions at positions corresponding to positions 171, 173, 175, 179 and 180, such as those described above.

In another aspect, the variant comprises one or more (several) substitutions selected from the group consisting of S171 {W, K, E}, S173 {P}, S175 {A, V, P} or G179 {C, V, Q, S, T, E, H, K, M, N}. In another aspect the variants mentioned above further comprise the substitution F180Y.

In another aspect, the variant comprises the substitutions S171W+S173P of the polypeptide with SEQ ID NO: 3.

In another aspect, the variant comprises the substitutions S171K+S173P of the polypeptide with SEQ ID NO: 3.

In another aspect, the variant comprises the substitutions S171E+S173P of the polypeptide with SEQ ID NO: 3.

In another aspect, the variant comprises the substitutions S171W+S175A of the polypeptide with SEQ ID NO: 3.

In another aspect, the variant comprises the substitutions S171K+S175A of the polypeptide with SEQ ID NO: 3.

In another aspect, the variant comprises the substitutions S171E+S175A of the polypeptide with SEQ ID NO: 3.

In another aspect, the variant comprises the substitutions S171W+S175V of the polypeptide with SEQ ID NO: 3.

In another aspect, the variant comprises the substitutions S171K+S175V of the polypeptide with SEQ ID NO: 3.

In another aspect, the variant comprises the substitutions S171E+S175V of the polypeptide with SEQ ID NO: 3.

In another aspect, the variant comprises the substitutions S171W+S175P of the polypeptide with SEQ ID NO: 3.

In another aspect, the variant comprises the substitutions S171K+S175P of the polypeptide with SEQ ID NO: 3.

In another aspect, the variant comprises the substitutions S171E+S175P of the polypeptide with SEQ ID NO: 3.

In another aspect, the variant comprises the substitutions S171W+G179 {C, V, Q, S, T, E, H, K, M, N} of the polypeptide with SEQ ID NO: 3.

In another aspect, the variant comprises the substitutions S171K+G179 {C, V, Q, S, T, E, H, K, M, N} of the polypeptide with SEQ ID NO: 3.

In another aspect, the variant comprises the substitutions S171E+G179 {C, V, Q, S, T, E, H, K, M, N} of the polypeptide with SEQ ID NO: 3.

In another aspect, the variant comprises the substitutions S171W+F180Y of the polypeptide with SEQ ID NO: 3.

In another aspect, the variant comprises the substitutions S171K+F180Y of the polypeptide with SEQ ID NO: 3.

In another aspect, the variant comprises the substitutions S171E+F180Y of the polypeptide with SEQ ID NO: 3.

In another aspect, the variant comprises the substitutions S173P+S175A of the polypeptide with SEQ ID NO: 3.

In another aspect, the variant comprises the substitutions S173P+S175V of the polypeptide with SEQ ID NO: 3.

In another aspect, the variant comprises the substitutions S173P+S175P of the polypeptide with SEQ ID NO: 3.

In another aspect, the variant comprises the substitutions S173P+G179 {C, V, Q, S, T, E, H, K, M, N} of the polypeptide with SEQ ID NO: 3.

In another aspect, the variant comprises the substitutions S173P+F180Y of the polypeptide with SEQ ID NO: 3.

In another aspect, the variant comprises the substitutions S175A+G179 {C, V, Q, S, T, E, H, K, M, N} of the polypeptide with SEQ ID NO: 3.

In another aspect, the variant comprises the substitutions S175V+G179 {C, V, Q, S, T, E, H, K, M, N} of the polypeptide with SEQ ID NO: 3.

In another aspect, the variant comprises the substitutions S175P+G179 {C, V, Q, S, T, E, H, K, M, N} of the polypeptide with SEQ ID NO: 3.

In another aspect, the variant comprises the substitutions S175A+F180Y of the polypeptide with SEQ ID NO: 3.

In another aspect, the variant comprises the substitutions S175V+F180Y of the polypeptide with SEQ ID NO: 3.

In another aspect, the variant comprises the substitutions S175P+F180Y of the polypeptide with SEQ ID NO: 3.

In another aspect, the variant comprises the substitutions G179 {C, V, Q, S, T, E, H, K, M, N}+F180Y of the polypeptide with SEQ ID NO: 3.

In another aspect, the variant comprises the substitutions S171W+S173P+S175A of the polypeptide with SEQ ID NO: 3.

In another aspect, the variant comprises the substitutions S171W+S173P+S175V of the polypeptide with SEQ ID NO: 3.

In another aspect, the variant comprises the substitutions S171W+S173P+S175P of the polypeptide with SEQ ID NO: 3.

In another aspect, the variant comprises the substitutions S171K+S173P+S175A of the polypeptide with SEQ ID NO: 3.

In another aspect, the variant comprises the substitutions S171K+S173P+S175V of the polypeptide with SEQ ID NO: 3.

In another aspect, the variant comprises the substitutions S171K+S173P+S175P of the polypeptide with SEQ ID NO: 3.

In another aspect, the variant comprises the substitutions S171E+S173P+S175A of the polypeptide with SEQ ID NO: 3.

In another aspect, the variant comprises the substitutions S171E+S173P+S175V of the polypeptide with SEQ ID NO: 3.

In another aspect, the variant comprises the substitutions S171E+S173P+S175P of the polypeptide with SEQ ID NO: 3.

In another aspect, the variant comprises the substitutions S171W+S173P+G179 {C, V, Q, S, T, E, H, K, M, N} of the polypeptide with SEQ ID NO: 3.

In another aspect, the variant comprises the substitutions S171K+S173P+G179 {C, V, Q, S, T, E, H, K, M, N} of the polypeptide with SEQ ID NO: 3.

In another aspect, the variant comprises the substitutions S171E+S173P+G179 {C, V, Q, S, T, E, H, K, M, N} of the polypeptide with SEQ ID NO: 3.

In another aspect, the variant comprises the substitutions S171W+S173P+F180Y of the polypeptide with SEQ ID NO: 3.

In another aspect, the variant comprises the substitutions S171K+S173P+F180Y of the polypeptide with SEQ ID NO: 3.

In another aspect, the variant comprises the substitutions S171E+S173P+F180Y of the polypeptide with SEQ ID NO: 3.

In another aspect, the variant comprises the substitutions S173P+S175A+G179 {C, V, Q, S, T, E, H, K, M, N} of the polypeptide with SEQ ID NO: 3.

In another aspect, the variant comprises the substitutions S173P+S175V+G179 {C, V, Q, S, T, E, H, K, M, N} of the polypeptide with SEQ ID NO: 3.

In another aspect, the variant comprises the substitutions S173P+S175P+G179 {C, V, Q, S, T, E, H, K, M, N} of the polypeptide with SEQ ID NO: 3.

In another aspect, the variant comprises the substitutions S173P+S175A+F180Y of the polypeptide with SEQ ID NO: 3.

In another aspect, the variant comprises the substitutions S173P+S175V+F180Y of the polypeptide with SEQ ID NO: 3.

In another aspect, the variant comprises the substitutions S173P+S175P+F180Y of the polypeptide with SEQ ID NO: 3.

In another aspect, the variant comprises the substitutions S175A+G179 {C, V, Q, S, T, E, H, K, M, N}+F180Y of the polypeptide with SEQ ID NO: 3.

In another aspect, the variant comprises the substitutions S175V+G179 {C, V, Q, S, T, E, H, K, M, N}+F180Y of the polypeptide with SEQ ID NO: 3.

In another aspect, the variant comprises the substitutions S175P+G179 {C, V, Q, S, T, E, H, K, M, N}+F180Y of the polypeptide with SEQ ID NO: 3.

In another aspect, the variant comprises the substitutions S171W+S173P+S175A+G179 {C, V, Q, S, T, E, H, K, M, N} of the polypeptide with SEQ ID NO: 3.

In another aspect, the variant comprises the substitutions S171K+S173P+S175A+G179 {C, V, Q, S, T, E, H, K, M, N} of the polypeptide with SEQ ID NO: 3.

In another aspect, the variant comprises the substitutions S171E+S173P+S175A+G179 {C, V, Q, S, T, E, H, K, M, N} of the polypeptide with SEQ ID NO: 3.

In another aspect, the variant comprises the substitutions S171W+S173P+S175V+G179 {C, V, Q, S, T, E, H, K, M, N} of the polypeptide with SEQ ID NO: 3.

In another aspect, the variant comprises the substitutions S171K+S173P+S175V+G179 {C, V, Q, S, T, E, H, K, M, N} of the polypeptide with SEQ ID NO: 3.

In another aspect, the variant comprises the substitutions S171E+S173P+S175V+G179 {C, V, Q, S, T, E, H, K, M, N} of the polypeptide with SEQ ID NO: 3.

In another aspect, the variant comprises the substitutions S171W+S173P+S175P+G179 {C, V, Q, S, T, E, H, K, M, N} of the polypeptide with SEQ ID NO: 3.

In another aspect, the variant comprises the substitutions S171K+S173P+S175P+G179 {C, V, Q, S, T, E, H, K, M, N} of the polypeptide with SEQ ID NO: 3.

In another aspect, the variant comprises the substitutions S171E+S173P+S175P+G179 {C, V, Q, S, T, E, H, K, M, N} of the polypeptide with SEQ ID NO: 3.

In another aspect, the variant comprises the substitutions S171W+S173P+S175V+F180Y of the polypeptide with SEQ ID NO: 3.

In another aspect, the variant comprises the substitutions S171K+S173P+S175V+F180Y of the polypeptide with SEQ ID NO: 3.

In another aspect, the variant comprises the substitutions S171E+S173P+S175V+F180Y of the polypeptide with SEQ ID NO: 3.

In another aspect, the variant comprises the substitutions S171W+S173P+S175P+F180Y of the polypeptide with SEQ ID NO: 3.

In another aspect, the variant comprises the substitutions S171K+S173P+S175P+F180Y of the polypeptide with SEQ ID NO: 3.

In another aspect, the variant comprises the substitutions S171E+S173P+S175P+F180Y of the polypeptide with SEQ ID NO: 3.

In another aspect, the variant comprises the substitutions S171W+S173P+S175A+G179 {C, V, Q, S, T, E, H, K, M, N}+F180Y of the polypeptide with SEQ ID NO: 3.

In another aspect, the variant comprises the substitutions S171K+S173P+S175A+G179 {C, V, Q, S, T, E, H, K, M, N}+F180Y of the polypeptide with SEQ ID NO: 3.

In another aspect, the variant comprises the substitutions S171E+S173P+S175A+G179 {C, V, Q, S, T, E, H, K, M, N}+F180Y of the polypeptide with SEQ ID NO: 3.

In another aspect, the variant comprises the substitutions S171W+S173P+S175V+G179 {C, V, Q, S, T, E, H, K, M, N}+F180Y of the polypeptide with SEQ ID NO: 3.

In another aspect, the variant comprises the substitutions S171K+S173P+S175V+G179 {C, V, Q, S, T, E, H, K, M, N}+F180Y of the polypeptide with SEQ ID NO: 3.

In another aspect, the variant comprises the substitutions S171E+S173P+S175V+G179 {C, V, Q, S, T, E, H, K, M, N}+F180Y of the polypeptide with SEQ ID NO: 3.

In another aspect, the variant comprises the substitutions S171W+S173P+S175P+G179 {C, V, Q, S, T, E, H, K, M, N}+F180Y of the polypeptide with SEQ ID NO: 3.

In another aspect, the variant comprises the substitutions S171K+S173P+S175P+G179 {C, V, Q, S, T, E, H, K, M, N}+F180Y of the polypeptide with SEQ ID NO: 3.

In another aspect, the variant comprises the substitutions S171E+S173P+S175P+G179 {C, V, Q, S, T, E, H, K, M, N}+F180Y of the polypeptide with SEQ ID NO: 3.

The variant may further comprise a substitution at one or more (several) other positions. For example, the variants may comprise an alteration at a position corresponding to positions selected from the group consisting of 39, 40, 70, 74, 81, 102, 121, 132, 137, 144, 155, 159, 162, 174, 176; 177, 241, 247, 256, 274, 286, 297. In one embodiment the variant comprises one of the following alterations: Y39D; T40{D,P}; Q70N, T74M; L81{F,H,V}; A102T; I121{V,T}; G132 {I,E}, I137{M; E}; S144{Q,R}; D155N; G159S; V162R; G174{S,T}; N176G; T177S; T241P; I247M; H256F; S274I; V286Q; T297P.

In another aspect, a variant in the detergent composition described herein comprises a substitution at one or more (e.g., several) positions corresponding to positions 171, 173, 175 or 179. In another aspect, a variant in the detergent composition described herein comprises a substitution at two positions corresponding to any of positions 171, 173, 175, 179 and 180. In another aspect, a variant in the detergent composition described herein comprises a substitution at three positions corresponding to any of positions 171, 173, 175, 179 and 180. In another aspect, a variant in the detergent composition described herein comprises a substitution at four positions corresponding to any of positions 171, 173, 175, 179 and 180. In another aspect, a variant in the detergent composition described herein comprises a substitution at each position corresponding to positions 171, 173, 175, 179 and 180.

The variants may further comprise one or more additional alterations at one or more (e.g., several) other positions. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Asn/Gln, Thr/Ser, Ala/Gly, Ala/Thr, Ser/Asn, Ala/Val, Ser/Gly, Tyr/Phe, Ala/Pro, Lys/Arg, Asp/Asn, Glu/Gln, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

For example, the variants may comprise an substitution at a position corresponding to any of the positions 171, 173, 175 or 179 and further comprises an alteration at any of the positions selected from the group consisting of positions 39, 40, 70, 74, 81, 102, 121, 132, 137, 144, 155, 159, 162, 174, 176; 177, 180, 241, 247, 256, 274, 286, 297. In an exemplary embodiment the alteration at any of the positions selected from the group consisting of 39, 40, 70, 74, 81, 102, 121, 132, 137, 144, 155, 159, 162, 174, 176, 177, 180, 241, 247, 256, 274, 286, 297 is a substitution. In a particular embodiment the variants in the detergent composition described herein comprise any of the following substitutions S171 {W, K, E}, S173P, S175 {A, V, P} or G179 {C, V, Q, S, T, E, H, K, M, N} of SEQ ID NO: 3, wherein the variant further comprises one or more substitution selected from the group consisting of: Y39D; T40{D,P}; Q70N, T74M; L81{F,H, V}; A102T; I121{V,T}; G132 {I,E}, I137{M; E}; S144{Q, R}, D155N; G159S; V162R; G174{S,T}; N176G; T177S; F180Y, T241P; I247M; H256F, S274I, V286Q; T297P.

In one embodiment, the detergent composition described herein comprises variants that comprise any of the following substitutions compared to SEQ ID NO. 3:

S171N S175P
I121V S175P
L81V S175P
A102T S175P
I137E S175P
S175A G179S
I121V S175A
L81F S175A
L81H S175A
L81V S175A
A102T S175A
I137E S175A
S144Q S175P
S144Q S175A

S144R G179Q
I121T S175P
S144R S171N
S144Q F180Y
S173P S274I
I137M S173P
S171N S173P
L81F S173P
L81H S173P
A102T S173P
S144Q S173P
I137E S173P
S173P S175P F180Y
S173Y G174S S175A F180Y
S173P G174T S175V T177S F180Y
S173P G174K S175P N176G T177S F180Y
S173P T241P
G179S F180Y G183A A187V
S173Y G174S S175A F180Y T241P
D155N G159S S173Y G174S S175A F180Y
S173Y G174S S175A F180Y S274I
S173Y G174S S175A F180Y V286Q
T40D S173Y G174S S175A F180Y
V162R S173P G174T S175V T177S F180Y
I121V S173P G174T S175V T177S F180Y
L81V S173P G174T S175V T177S F180Y
A102T S173P G174T S175V T177S F180Y
S173P G174T S175V T177S F180Y T241P
I137E S173P G174T S175V T177S F180Y
S144Q S173P G174T S175V T177S F180Y
Q70N S173P G174T S175V T177S F180Y
D155N G159S S173P G174T S175V T177S F180Y
S173P G174T S175V T177S F180Y S274I
S173P G174T S175V T177S F180Y V286Q
T40D S173P G174T S175V T177S F180Y
S171N S173P G174T S175V T177S F180Y
V162R S173P G174K S175P N176G T177S F180Y
I121V S173P G174K S175P N176G T177S F180Y
L81V S173P G174K S175P N176G T177S F180Y
A102T S173P G174K S175P N176G T177S F180Y
S173P G174K S175P N176G T177S F180Y T241P
I137E S173P G174K S175P N176G T177S F180Y
S144Q S173P G174K S175P N176G T177S F180Y
Q70N S173P G174K S175P N176G T177S F180Y
D155N G159S S173P G174K S175P N176G T177S F180Y
S173P G174K S175P N176G T177S F180Y S274I
S173P G174K S175P N176G T177S F180Y V286Q
T40D S173P G174K S175P N176G T177S F180Y
S171N S173P G174K S175P N176G T177S F180Y
I121V I137E S173Y G174S S175A F180Y
L81V I137E S173Y G174S S175A F180Y
I137E S173Y G174S S175A F180Y T241P
Q70N I137E S173Y G174S S175A F180Y
I137E S173Y G174S S175A F180Y S274I
I137E S173Y G174S S175A F180Y T297P
I121V I137E S173P G174T S175V T177S F180Y
L81V I137E S173P G174T S175V T177S F180Y
I137E S173P G174T S175V T177S F180Y T241P
Q70N I137E S173P G174T S175V T177S F180Y
I137E S173P G174T S175V T177S F180Y V286Q
I137E S173P G174T S175V T177S F180Y T297P
I137E S171N S173P G174T S175V T177S F180Y
I137E S173P G174T S175A T177S F180Y
I121V I137E S173P G174K S175P N176G T177S F180Y
Q70N I137E S173P G174K S175P N176G T177S F180Y
I137E S173P G174K S175P N176G T177S F180Y S274I
I137E S173P G174K S175P N176G T177S F180Y V286Q
I137E S173P G174K S175P N176G T177S F180Y T297P
I137E S171N S173P G174K S175P N176G T177S F180Y
I137E S173P G174K S175A N176G T177S F180Y
V162R S173Y G174S S175A F180Y
A102T S173Y G174S S175A F180Y
G1321 S173P G174T S175V T177S F180Y
S173P G174T S175V T177S F180Y T297P
S173P G174T S175A T177S F180Y
S173P S175A
I137E S144Q S173Y G174S S175A F180Y
T40L I137E S173Y G174S S175A F180Y
I137E S173Y S175A F180Y
I137E S173P S175V T177S F180Y
I137E S173P S175P N176G T177S F180Y
S171N S173Y G174S S175A F180Y
S173P G174K S175A N176G T177S F180Y
I137E S173Y G174S S175A F180Y V286Q
I137E S173P G174T S175V T177S F180Y S274I
T74M I137E S173P
T79I I137E S173P
L81G S173P
L34I I137E S173P
Y39D I137E S173P
T40P I137E S173P
I137E S173P I247M
I137E S173P H256F
I137E S144Q S173P G174T S175V T177S F180Y
I137E S144Q S173P G174K S175P N176G T177S F180Y
S173Y G174S A175P F180Y
I137E S173Y G174S A175P F180Y
S173P G174T V175P T177S F180Y
I137E S173P G174T V175P T177S F180Y
I137E S173P G174T V175P T177S F180Y T297P
V162R S171N S173P G174K S175P N176G T177S F180Y
I137E S171N S173P G174K S175P N176G T177S F180Y T241P
I137E S171N S173P G174K S175P N176G T177S F180Y T297P
I137E S173P S175P F180Y
V162R S173P S175P F180Y
S173P S175P F180Y S274I
S173P S175P F180Y T241P
S173P S175P F180Y T297P
S173P S175P F180Y V286Q

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide. For TY-145 (SEQ ID NO: 3) the catalytic triad comprising the amino acids D35, H72 and S251 is essential for protease activity of the enzyme.

In an embodiment, the detergent composition comprises a protease variant wherein the variant has improved catalytic activity compared to the parent enzyme.

In an embodiment, the detergent composition comprises a protease variant wherein the variant has improved stability compared to the parent enzyme or compared to a protease having the identical amino acid sequence of said variant but not having a substitution at one or more of said specified positions or compared to a protease with SEQ ID NO: 3, wherein stability is measured in Example 2 as described in "Material and Methods" herein.

In an embodiment, a variant in the detergent composition described herein has improved stability compared to the parent enzyme or compared to a protease having the identical amino acid sequence of said variant but not having a substitution at one or more of said specified positions or compared to a protease with SEQ ID NO: 3.

Parent Proteases

Protease Variant

The term "variant" and the term "protease variant" are defined above.

Homologous Protease Sequences

The homology between two amino acid sequences is in this context described by the parameter "identity" for purposes herein, the degree of identity between two amino acid sequences is determined using the Needleman-Wunsch algorithm as described above. The output from the routine is besides the amino acid alignment the calculation of the "Percent Identity" between the two sequences.

Based on this description it is routine for a person skilled in the art to identify suitable homologous proteases, which can be modified according to embodiments herein.

Substantially homologous parent protease variants may have one or more (several) amino acid substitutions, deletions and/or insertions, in the present context the term "one or more" is used interchangeably with the term "several". These changes may be of a minor nature, that is conservative amino acid substitutions as described above and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, EMBO J. 4: 1075; Nilsson et al., 1991, Methods Enzymol. 198: 3. See, also, in general, Ford et al., 1991, Protein Expression and Purification 2: 95-107.

Although the changes described above may be of a minor nature, such changes may also be of a substantive nature such as fusion of larger polypeptides of up to 300 amino acids or more both as amino- or carboxyl-terminal extensions.

The parent protease may comprise or consist of the amino acid sequence of SEQ ID NO: 3 or an allelic variant thereof; or a fragment thereof having protease activity. In one aspect, the parent protease comprises or consists of the amino acid sequence of SEQ ID NO: 3.

The parent protease may be (a) a polypeptide having at least 70% sequence identity to the mature polypeptide of SEQ ID NO: 3; (b) a polypeptide encoded by a polynucleotide that hybridizes under medium or high stringency conditions with (i) the mature polypeptide coding sequence of SEQ ID NO: 1, (ii) a sequence encoding the mature polypeptide of SEQ ID NO: 2, or (iii) the full-length complement of (i) or (ii); or (c) a polypeptide encoded by a polynucleotide having at least 70% sequence identity to the mature polypeptide coding sequence of SEQ ID NO: 1.

In an aspect, the parent protease has a sequence identity to the polypeptide with SEQ ID NO: 3 of at least 70%, such as at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, e.g., at least 99.1%, at least 99.2%, at least 99.3%, at least 99.4%, at least 99.5%, at least 99.6%, or 100% sequence identity to the polypeptide with SEQ ID NO: 3, which have protease activity.

In one aspect, the amino acid sequence of the parent protease differs by no more than 10 amino acids, e.g., 1, 2, 3, 4, 5, 6, 7, 8, or 9, from the mature polypeptide with SEQ ID NO: 3.

In another aspect, the parent protease comprises or consists of the amino acid sequence of SEQ ID NO: 3. In another aspect, the parent protease comprises or consists of amino acids 1 to 311 of SEQ ID NO: 2.

In another aspect, the parent protease is encoded by a polynucleotide that hybridizes under very low stringency conditions, low stringency conditions, medium stringency conditions, or high stringency conditions, or very high stringency conditions with (i) the mature polypeptide coding sequence of SEQ ID NO: 1, (ii) a sequence encoding the mature polypeptide of SEQ ID NO: 2, or (iii) the full-length complement of (i) or (ii), (Sambrook et al., 1989, Molecular Cloning, A Laboratory Manual, 2d edition, Cold Spring Harbor, N.Y.).

The polynucleotide of SEQ ID NO: 1 or a subsequence thereof, as well as the polypeptide of SEQ ID NO: 3 or a fragment thereof may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. In an exemplary embodiment, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with 32P, 3H, 35S, biotin, or avidin). Such probes are encompassed by embodiments herein.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes herein, hybridization indicates that the polynucleotide hybridizes to a labeled nucleic acid probe corresponding to (i) SEQ ID NO: 1; (ii) the mature polypeptide coding sequence of SEQ ID NO: 1; (iii) a sequence encoding the mature polypeptide of SEQ ID NO: 2; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleotide acid probe is a 80 to 1140 nucleotides long fragment of SEQ ID NO: 1, e.g., 90, 100, 200, 300, 400, 500, 600, 700, 800, 900, 1000 or 1100 nucleotides long. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1 or a sequence encoding the mature polypeptide of SEQ ID NO: 2.

In another embodiment, the parent is encoded by a polynucleotide having a sequence identity to the mature polypeptide coding sequence of SEQ ID NO: 1 or a sequence encoding the mature polypeptide of SEQ ID NO: 2 wherein the polynucleotide has at least 70%, e.g., at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, e.g., at least 99.1%, at least 99.2%, at least 99.3%, at least 99.4%, at least 99.5%, at least 99.6%, or 100% sequence identity to the mature polypeptide coding sequence of SEQ ID NO: 1 or a sequence encoding the mature polypeptide of SEQ ID NO: 2.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of embodiments herein. A fusion polypeptide is produced by fusing a polynucleotide encoding another polypeptide to a polynucleotide of embodiments herein. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, *Drug Discovery World* 4: 35-48.

The parent may be obtained from organisms of any genus. For purposes herein, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial protease. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* protease, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* protease.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* protease In one aspect, the parent is a *Bacillus* sp. protease, e.g., the protease with SEQ ID NO: 3 or the mature polypeptide of SEQ ID NO 2.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

Embodiments herein also relate to methods for producing a detergent composition comprising the step of adding a protease variant obtained by a method for obtaining said protease variant, comprising introducing into a parent protease a substitution at one or more positions corresponding to positions 171, 173, 175 or 179 of SEQ ID NO: 3, wherein the variant has an amino acid sequence which is at least 70% identical to SEQ ID NO: 3, and recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., U.S. Patent Application Publication No. 2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used in the embodiments herein. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409, WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Thus, embodiments herein also relate to a method for obtaining a protease variant, comprising introducing into a parent protease a substitution at one or more positions corresponding to positions 171, 173, 175 or 179 of SEQ ID NO: 3; and recovering the variant.

Another embodiment concerns a method for producing a detergent composition comprising the step of adding a protease variant obtained by a method for obtaining a protease variant, comprising substitution of one or more amino acids in the loop corresponding to positions 171, 173, 175 or 179 of SEQ ID NO: 3, especially a method as described above, wherein the parent protease is selected from the group consisting of a polypeptide having at least 70% sequence identity to SEQ ID NO: 3;

a. a polypeptide encoded by a polynucleotide that hybridizes under medium or high stringency conditions with (i) the mature polypeptide coding sequence of SEQ ID NO: 1, (ii) a sequence encoding the mature polypeptide of SEQ ID NO: 2, or (iii) the full-length complement of (i) or (ii);

b. a polypeptide encoded by a polynucleotide having at least 70% identity to the mature polypeptide coding sequence of SEQ ID NO: 1 or a sequence encoding the mature polypeptide of SEQ ID NO: 2; and c. a fragment of the mature polypeptide of SEQ ID NO: 2, which has protease activity.

The aspects of embodiments described above for the detergent composition are also aspects of the method for producing a detergent composition.

Thus a particular aspect concerns a method for obtaining a protease variant, comprising introducing into a parent protease a substitution of one or more amino acids in the loop corresponding to positions 171, 173, 175 or 179 of SEQ ID NO: 3, wherein the substitution(s) is/are performed in SEQ ID NO: 3, and wherein the substitutions are selected from the group consisting of S171 {W, K, E}, S173 {P}, S175 {A, V, P} or G179 {C, V, Q, S, T, E, H, K, M, N}. Additionally a further substitution can be introduced at position corresponding to 180 of SEQ ID NO:3, especially the substitution is F180Y.

One aspect relates to methods for producing a detergent composition comprising the step of adding a protease variant obtained by a method of producing the variants, wherein the method comprises substitution of at least one amino acid in the loop corresponding to positions 171, 173, 175 or 179 of SEQ ID NO: 3, wherein (a) the variant has a sequence identity to SEQ ID NO: 3 of at least 70% and less than 100% and (b) the variant has protease activity.

In one embodiment the variant produced according to said method comprises a substitution at a position corresponding to position 171 of SEQ ID NO: 3 and further comprises a substitution at one or more positions corresponding to positions 173, 175, 179 and 180 of SEQ ID NO: 3.

In one embodiment the variant produced according to said method comprises a substitution at a position corresponding to position 173 of SEQ ID NO: 3 and further comprises a substitution at one or more positions corresponding to positions 171, 175, 179 and 180 of SEQ ID NO: 3.

In one embodiment the variant produced according to said method comprises a substitution at a position corresponding to position 175 of SEQ ID NO: 3 and further comprises a substitution at one or more positions corresponding to positions 171, 173, 179 and 180 of SEQ ID NO: 3.

In one embodiment the variant produced according to said method comprises a substitution at a position corresponding to position 179 of SEQ ID NO: 3 and further comprises a substitution at one or more positions corresponding to positions 171, 173, 175 and 180 of SEQ ID NO: 3.

In one embodiment the variant produced according to said method comprises a substitution at a position corresponding to position 180 of SEQ ID NO: 3 and further comprises a substitution at one or more positions corresponding to positions 171, 173, 175 and 179 of SEQ ID NO: 3.

In one embodiment the variant produced according to said method comprises a substitution at a position corresponding to position 171 of SEQ ID NO: 3 with an amino acid selected from {W, K, E}.

In one embodiment the variant produced according to said method comprises a substitution at a position corresponding to position 173 of SEQ ID NO: 3 with P.

In one embodiment the variant produced according to said method comprises a substitution at a position corresponding to position 175 of SEQ ID NO: 3 with an amino acid selected from {A, V, P}.

In one embodiment the variant produced according to said method comprises a substitution at a position corresponding to position 179 of SEQ ID NO: 3 with an amino acid selected from {C, V, Q, S, T, E, H, K, M, N}.

The variant produced according to said method may further comprise a substitution at a position corresponding to position 180 of SEQ ID NO: 3 with Y.

A further aspect of embodiments herein is a detergent composition obtained by a method described above and its use.

Compositions

In one certain aspect the variants in the detergent composition described herein has improved stability in detergents compared to the parent enzyme or compared to a protease having the identical amino acid sequence of said variant but not having the substitutions at one or more of said specified positions or compared to a protease with SEQ ID NO 3, wherein stability is measured in Example 2 as described in "Material and Methods" herein.

Thus, in an exemplary embodiment the composition is a detergent composition, and one aspect relates to the use of a detergent composition comprising a variant in the detergent composition described herein in a cleaning process such as laundry or hard surface cleaning.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Enzyme in the Detergent Composition

In one embodiment, the variants in the detergent composition may be added in an amount (in mg per liter of wash liquor) corresponding to from about 0.001 to about 100 mg of protein, such as from about 0.01 to about 100 mg of protein, such as from about 0.005 to about 50 mg of protein, such as from about 0.01 to about 25 mg of protein, such as from about 0.05 to about 10 mg of protein, or from about 0.05 to about 5 mg of protein, per liter of wash liquor.

In a further aspect, the detergent composition described herein contains a stabilizing agent. In an exemplary embodiment the stabilizing agent is selected from the group consisting of a polyol, such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid.

The composition may be formulated as described in, for example, WO92/19709 and WO92/19708 or the variants in the detergent composition described herein may be stabilized using peptide aldehydes or ketones such as described in WO2005/105826 and WO2009/118375.

In an exemplary embodiment, the detergent composition comprises two or more stabilizing agents selected from the group containing propylene glycol, glycerol, a sugar, a sugar alcohol, lactid acid, boric acid, borate, a phenyl boronic acid derivate.

In an exemplary embodiment, the residue R in the phenylboronic acid derivative is a C1-C6 alkyl group, such as $CH_3$, $CH_3CH_2$ or $CH_3CH_2CH_2$. In another embodiment, the residue R in the phenylboronic acid derivative is hydrogen.

In another exemplary embodiment, the phenylboronic acid derivative is 4-formylphenylboronic acid (4-FPBA). It is given in the following formula:

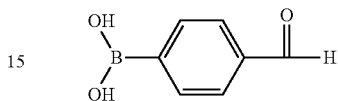

Phenylboronic acid derivatives described herein can furthermore have other chemical modifications on the phenyl ring, and in particular they can contain one or more methyl, amino, nitro, chloro, fluoro, bromo, hydroxyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethylchroman-6-sulfonyl residues or groups or combinations thereof.

All stabilizing agents described herein can be present in the detergent composition in all protonated or deprotonated forms. Furthermore, all such compounds, in particular their deprotonated forms, can be associated with cations. Exemplary cations in this respect are monovalent or polyvalent, in particular divalent, cations, in particular Na ions (Na+), K ions (K+), Li ions (Li+), Ca ions (Ca2+), Mg ions (Mg2+), Mn ions (Mn2+) and Zn ions (Zn2+). Of particular interest are Na ions (Na+). An exemplary detergent composition described herein comprises two or more stabilizing agents selected from the group consisting of propylene glycol, glycerol, 4-formylphenyl boronic acid and borate.

In an exemplary embodiment, the detergent composition comprises 4-formylphenyl boronic acid and/or borate.

In an exemplary embodiment, the phenylboronic acid derivative is contained in the detergent composition described herein in a quantity of from about 0.00001 to about 5.0 wt. %, such as from about 0.0001 to about 3.0 wt. %, from about 0.001 to about 2.0 wt. %, from about 0.005 to about 1.0 wt. %, from about 0.01 to about 0.5 wt. %, or from about 0.02 to about 0.3 wt. %, in the detergent composition, In an exemplary embodiment, the boric acid/borate is contained in a quantity of from about 0.001 to about 5.5 wt. %, such as from about 0.01 to about 4.5 wt. %, from about 0.05 to about 3.5, from about 0.1 to about 3, from about 0.4 to about 2.49, or from about 0.5 to about 1.5 wt. %, in the detergent composition.

Addition of a combination of borate and 4-formylphenyl boronic acid has been found to be particularly effective, leading to a high increase in enzyme stability in the detergent composition.

In an exemplary embodiment, the boric acid/borate is contained in a quantity of from about 0.001 to about 5.5 wt. %, such as from about 0.075 to about 4.5 wt. %, from about 0.09 to about 3.5, or from about 0.1 to about 2.49 wt. %, and the phenylboronic acid derivative is contained in a quantity of from about 0.001 to about 0.08 wt. %, such as from about 0.003 to about 0.06 wt. %, from about 0.005 to about 0.05 wt. %, from about 0.007 to about 0.03 wt. %, or from about 0.009 to about 0.01 wt. %, in the detergent composition.

A particular embodiment includes the addition of 4-formylphenyl boronic acid in an amount of from about 1.0 to about 2.0 wt. % in combination with about 1.0 wt. % borate.

A variant of embodiments herein may also be incorporated in the detergent formulations disclosed in WO97/07202, which is hereby incorporated by reference.

The detergent composition described herein may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In an exemplary embodiment, the detergent composition described herein is a laundry detergent composition or a dishwashing composition, such as a machine dishwashing composition.

In another embodiment, the detergent composition described herein is a liquid detergent composition.

A exemplary liquid detergent composition for said washing system has the following composition (all indications in percentage by weight): 0.3 to 0.5% xanthan gum, 0.2 to 0.4% antifoaming agent, 6 to 7% glycerol, 0.3 to 0.5% ethanol, 4 to 7% FAEOS (fatty alcohol ether sulfate), 24 to 28% nonionic surfactants, 1% boric acid, 1 to 2% sodium citrate (dihydrate), 2 to 4% soda, 14 to 16% coconut fatty acid, 0.5% HEDP (1-hydroxyethane-(1,1-diphosphonic acid)), 0 to 0.4% PVP (polyvinylpyrrolidone), 0 to 0.05% optical brighteners, 0 to 0.001% dye, remainder deionized water. An exemplary dosing ratio of the liquid washing agent is from about 4.5 to about 6.0 grams per liter of washing liquor, for example about 4.7, about 4.9, or about 5.9 grams per liter of washing liquor. In an exemplary embodiment, washing occurs in a pH range of from about pH 8 to about pH 10.5, such as from about pH 8 to about pH 9.

An exemplary powdered detergent composition for said washing system has the following composition (all indications in percentage by weight): 10% linear alkylbenzenesulfonate (sodium salt), 1.5% C12 to C18 fatty alcohol sulfate (sodium salt), 2.0% C12 to C18 fatty alcohol with 7 EO, 20% sodium carbonate, 6.5% sodium hydrogencarbonate, 4.0% amorphous sodium disilicate, 17% sodium carbonate peroxohydrate, 4.0% TAED, 3.0% polyacrylate, 1.0% carboxymethyl cellulose, 1.0% phosphonate, 25% sodium sulfate; remainder: optionally foam inhibitors, optical brighteners, scents, and if applicable water to make 100%. An exemplary dosing ratio of the powdered washing agent is from about 5.5 to about 7.0 grams per liter of washing liquor, for example about 5.6, about 5.9, or about 6.7 grams per liter of washing liquor. In an exemplary embodiment, washing occurs in a pH range of from about pH 9 to about pH 11.

A detergent composition according to embodiments herein might further comprise one or more peroxy compounds.

Such peroxy compounds optionally present in the compositions which may in particular be considered are organic peracids or peracidic salts of organic acids, such as phthalimidopercaproic acid, perbenzoic acid or salts of diperdodecanedioic acid, hydrogen peroxide and inorganic salts which release hydrogen peroxide under the washing conditions, such as perborate, percarbonate and/or persilicate. Hydrogen peroxide may here also be produced with the assistance of an enzymatic system, i.e. an oxidase and its substrate. Where solid peroxy compounds are to be used, they may be used in the form of powders or granules, which may also in principle be encapsulated in known manner. Alkali metal percarbonate, alkali metal perborate monohydrate, alkali metal perborate tetrahydrate or hydrogen peroxide in the form of aqueous solutions containing from about 3 wt. % to about 10 wt. % of hydrogen peroxide are suitable. Peroxy compounds may be present in washing or cleaning agents described herein in quantities of up to about 50 wt. %, in particular from about 5 wt. % to about 30 wt. %.

Apart from the protease variant to be used according to embodiments herein, the detergent compositions described herein, which may in particular take the form of pulverulent solids, post-compressed particles, homogeneous solutions or suspensions, may in principle contain any ingredients known and conventional in such compositions. The detergent compositions described herein may in particular contain builder substances, surface-active surfactants, water-miscible organic solvents, enzymes, sequestering agents, electrolytes, pH regulators, polymers with specific effects, such as soil release polymers, dye transfer inhibitors, graying inhibitors, crease-reducing polymeric active ingredients and shape-retaining polymeric active ingredients, and further auxiliary substances, such as optical brighteners, foam regulators, additional peroxy activators, colorants and scents.

In addition to the above-stated ingredients, a composition according to embodiments herein may contain conventional antimicrobial active ingredients in order to enhance the disinfection action, for example towards specific microorganisms. Such antimicrobial additives may be present in the disinfectants described herein in quantities of up to about 10 wt. %, in particular from about 0.1 wt. % to about 5 wt. %.

In a detergent composition according embodiments herein, conventional bleach activators which form peroxycarboxylic acid or peroxyimidic acids under perhydrolysis conditions and/or conventional bleach-activating transition metal complexes may also be used. The bleach activator component optionally present in particular in quantities of 0.5 wt. % to 6 wt. % comprises conventionally used N- or O-acyl compounds, for example polyacylated alkylenediamines, in particular tetraacetylethylenediamine, acylated glycolurils, in particular tetraacetylglycoluril, N-acylated hydantoins, hydrazides, triazoles, urazoles, diketopiperazines, sulfurylamides and cyanurates, moreover carboxylic anhydrides, in particular phthalic anhydride, carboxylic acid esters, in particular sodium isononanoylphenolsulfonate, and acylated sugar derivatives, in particular pentaacetyl glucose, together with cationic nitrile derivatives such as trimethylammonium acetonitrile salts. In order to avoid interaction with per compounds during storage, the bleach activators may in known manner have been coated with shell substances or granulated, particularly suitable options being tetraacetylethylenediamine granulated with the assistance of carboxymethylcellulose and having an average grain size of 0.01 mm to 0.8 mm, granulated 1,5-diacetyl-2,4-dioxohexahydro-1,3,5-triazine, and/or trialkylammonium acetonitrile formulated in particulate form. Such bleach activators may be present in washing or cleaning compositions in quantities of up to about 8 wt. %, in particular from about 2 wt. % to about 6 wt. %, in each case relative to entire composition.

The compositions described herein may contain one or more surfactants, with anionic surfactants, nonionic surfactants and mixtures thereof in particular being considered, but cationic and/or amphoteric surfactants also possibly being present. Suitable nonionic surfactants are in particular alkyl glycosides and ethoxylation and/or propoxylation products of alkyl glycosides or linear or branched alcohols in each case having 12 to 18 C atoms in the alkyl moiety and 3 to 20, such as 4 to 10, alkyl ether groups. Corresponding ethoxylation and/or propoxylation products of N-alkylamines, vicinal diols, fatty acid esters and fatty acid amides, which correspond with regard to the alkyl moiety to the stated long-chain alcohol derivatives, and of alkylphenols having 5 to 12 C atoms in the alkyl residue may furthermore be used.

Suitable anionic surfactants are in particular soaps and those which contain sulfate or sulfonate groups, such as with alkali metal ions as cations. Usable soaps include the alkali metal salts of saturated or unsaturated fatty acids with 12 to 18 C atoms. Such fatty acids may also be used in incompletely neutralized form. Usable surfactants of the sulfate type include the salts of sulfuric acid semiesters of fatty alcohols with 12 to 18 C atoms and the sulfation products of the stated nonionic surfactants with a low degree of ethoxylation. Usable surfactants of the sulfonate type include linear alkylbenzene sulfonates with 9 to 14 C atoms in the alkyl moiety, alkanesulfonates with 12 to 18 C atoms, and olefin sulfonates with 12 to 18 C atoms, which arise from the reaction of corresponding monoolefins with sulfur trioxide, and alpha-sulfofatty acid esters which arise from the sulfonation of fatty acid methyl or ethyl esters.

Such surfactants are present in the washing compositions according to embodiments herein in proportions of from about 5 wt. % to about 50 wt. %, in particular from about 8 wt. % to about 30 wt. %, while exemplary disinfectants according to embodiments herein and exemplary cleaning compositions according to embodiments herein contain from about 0.1 wt. % to about 20 wt. %, in particular from about 0.2 wt. % to about 5 wt. % of surfactants.

The compositions described herein, in particular if they are compositions intended for treating textiles, may in particular contain one or more of the cationic, textile-softening substances of the general formulae X, XI, or XII as cationic active substances with a textile-softening action:

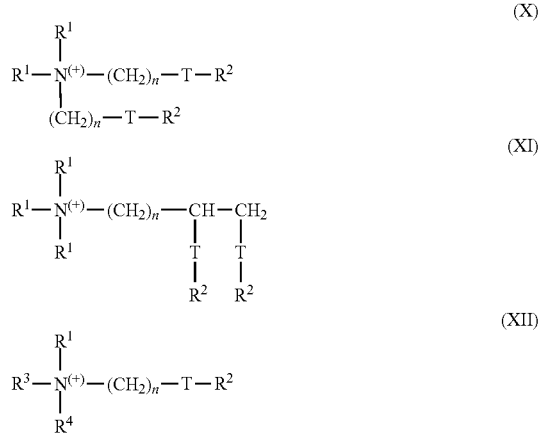

in which each group R1 is mutually independently selected from among C1-6 alkyl, alkenyl or hydroxyalkyl groups; each group R2 is mutually independently selected from among C8-28 alkyl or alkenyl groups; R3=R1 or (CH2)n-T-R2; R4=R1 or R2 or (CH2)n-T-R2; T=—CH2-, —O—CO— or —CO—O— and n is an integer from 0 to 5.

The cationic surfactants comprise conventional anions of a nature and number required for charge balancing, it being possible to select said anions not only from, for example, halides but also from anionic surfactants. In exemplary embodiments, cationic surfactants which may be used are hydroxyalkyltrialkylammonium compounds, in particular C12-18 alkyl(hydroxyethyl)dimethylammonium compounds, and the halides thereof, in particular chlorides. An exemplary composition contains from about 0.5 wt. % to about 25 wt. %, in particular from about 1 wt. % to about 15 wt. % of cationic surfactant.

An exemplary composition contains at least one water-soluble and/or water-insoluble, organic and/or inorganic builder. Water-soluble organic builder substances include polycarboxylic acids, in particular citric acid and saccharic acids, monomeric and polymeric aminopolycarboxylic acids, in particular methylglycinediacetic acid, nitrilotriacetic acid and ethylenediaminetetraacetic acid together with polyaspartic acid, polyphosphonic acids, in particular aminotris(methylenephosphonic acid), ethylenediamine-tetrakis(methylenephosphonic acid) and 1-hydroxyethane-1,1-diphosphonic acid, polymeric hydroxyl compounds such as dextrin and polymeric (poly-)carboxylic acids, in particular polycarboxylates obtainable by oxidizing polysaccharides or dextrins, and/or polymeric acrylic acids, methacrylic acids, maleic acids and copolymers thereof, which may also contain small proportions of polymerizable substances without carboxylic acid functionality. The relative molecular mass of the homopolymers of unsaturated carboxylic acids is in general from about 5,000 to about 200,000, that of the copolymers from about 2,000 to about 200,000, such as from about 50,000 to about 120,000, in each case relative to free acid. One particularly suitable acrylic acid/maleic acid copolymer has a relative molecular mass of from about 50,000 to about 100,000. Suitable, albeit less preferred, compounds of this class are copolymers of acrylic acid or methacrylic acid with vinyl ethers, such as vinyl methyl ethers, vinyl esters, ethylene, propylene and styrene, the acid fraction of which amounts to at least 50 wt. %. Terpolymers containing as monomers two unsaturated acids and/or the salts thereof and, as third monomer, vinyl alcohol and/or an esterified vinyl alcohol or a carbohydrate may also be used as water-soluble organic builder substances. an exemplary first acidic monomer or the salt thereof is derived from a monoethylenically unsaturated C3-C8 carboxylic acid and from a C3-C4 monocarboxylic acid, in particular from (meth) acrylic acid. An exemplary second acidic monomer or the salt thereof may be a derivative of a C4-C8 dicarboxylic acid, such as maleic acid, and/or a derivative of an allylsulfonic acid which is substituted in position 2 with an alkyl or aryl residue. Such polymers generally have a relative molecular mass of from about 1,000 to about 200,000. Further exemplary copolymers are those which comprise acrolein and acrylic acid/acrylic acid salts or vinyl acetate as monomers. The organic builder substances may be used, in particular for producing liquid compositions, in the form of aqueous solutions, such as in the form of from about 30 to about 50 wt. % aqueous solutions. All the stated acids are generally used in the form of the water-soluble salts, in particular the alkali metal salts, thereof.

Such organic builder substances may, if desired, be present in quantities of up to about 40 wt. %, in particular of up to about 25 wt. %, such as from about 1 wt. % to about 8 wt. %. Quantities close to the stated upper limit are used in pasty or liquid, in particular water-containing, compositions according to embodiments herein.

Water-soluble inorganic builder materials which may in particular be considered are polymeric alkali metal phosphates, which may be present in the form of the alkaline, neutral or acidic sodium or potassium salts thereof. Examples are tetrasodium diphosphate, disodium dihydrogen diphosphate, pentasodium triphosphate, "sodium hexametaphosphate" and the corresponding potassium salts or mixtures of sodium and potassium salts. Water-insoluble, water-dispersible inorganic builder materials which are used are in particular crystalline or amorphous alkali metal aluminosilicates, in quantities of up to about 50 wt. %, such as no more than about 40 wt. % and, in liquid compositions, in particular from about 1 wt. % to about 5 wt. %. Among these, washing composition grade crystalline sodium aluminosilicates, in particular zeolite A, P and optionally X, are suitable. Quantities close to the stated upper limit may be used in solid, particulate compositions. Suitable aluminosilicates in particular comprise no particles with a grain size of above about 30 μm and may consist to an extent of at least about 80 wt. % of particles with a size below about 10 μm. Their calcium binding capacity, which may be determined as stated in German patent DE 24 12 837, is generally in the range of from about 100 to about 200 mg of CaO per gram.

Suitable substitutes or partial substitutes for the stated aluminosilicate are crystalline alkali metal silicates, which may be present alone or mixed with amorphous silicates. Exemplary alkali metal silicates usable as builders in the compositions described herein have a molar ratio of alkali metal oxide to SiO2 of below about 0.95, in particular of from about 1:1.1 to about 1:12 and may be in amorphous or crystalline form. Exemplary alkali metal silicates are sodium silicates, in particular amorphous sodium silicates, with a molar ratio $Na_2O:SiO_2$ of from about 1:2 to about 1:2.8. Exemplary crystalline silicates, which may be present alone or mixed with amorphous silicates, are crystalline phyllosilicates of the general formula $Na_2Si_xO_{2x+i} \cdot y\ H_2O$, in which x, the "modulus", is a number from about 1.9 to about 4 and y is a number from 0 to 20 and exemplary values for x are 2, 3 or 4. Exemplary crystalline phyllosilicates are those in which x in the stated general formula assumes the values 2 or 3. In particular, both β- and δ-sodium disilicates ($Na_2Si_2O_5 \cdot y\ H_2O$) are preferred. Virtually anhydrous crystalline alkali metal silicates, produced from amorphous alkali metal silicates, of the above-stated general formula in which x means a number from 1.9 to 2.1 may also be used in compositions described herein. A crystalline sodium phyllosilicate with a modulus of 2 to 3, as may be produced from sand and soda, is used in an exemplary embodiment of compositions. Crystalline sodium silicates with a modulus in the range from 1.9 to 3.5 are used in a further embodiment of compositions. In one development of compositions, a granular compound of alkali metal silicate and alkali metal carbonate is used, as is for example commercially available under the name Nabion® 15. If alkali metal aluminosilicate, in particular zeolite, is present as an additional builder substance in an embodiment, the weight ratio of aluminosilicate to silicate, in each case relative to anhydrous active substances, amounts to from about 1:10 to about 10:1. In compositions which contain both amorphous and crystalline alkali metal silicates, the weight ratio of amorphous alkali metal silicate to crystalline alkali metal silicate amounts to from about 1:2 to about 2:1 and in particular to from about 1:1 to about 2:1.

Builder substances are present in the exemplary washing or cleaning compositions in quantities of up to about 60 wt. %, in particular from about 5 wt. % to about 40 wt. %.

In an embodiment, a composition comprises a water-soluble "builder block". Use of the term "builder block" is intended to indicate that the composition does not contain any further builder substances as such which are water-soluble, i.e. all the builder substances present in the composition are combined in the "block" characterized in this manner, an exception being, however, made for the quantities of substances which may be present, as is conventional in commerce, in small quantities as contaminants or stabilizing additives in the other ingredients of the compositions. The term "water-soluble" should here be taken to mean that, at the concentration which is obtained under conventional conditions by the input quantity of the composition containing it, the builder block dissolves without leaving a residue. Exemplary compositions contain at least about 15 wt. % and up to about 55 wt. %, in particular from about 25 wt. % to about 50 wt. % of water-soluble builder block. The latter is composed of the components:

a) from about 5 wt. % to about 35 wt. % citric acid, alkali metal citrate and/or alkali metal carbonate, which may also at least in part be replaced by alkali metal hydrogencarbonate, b) up to about 10 wt. % alkali metal silicate with a modulus in the range from 1.8 to 2.5, c) up to about 2 wt. % phosphonic acid and/or alkali metal phosphonate, d) up to about 50 wt. % alkali metal phosphate, and e) up to about 10 wt. % polymeric polycarboxylate, the stated quantities relating to the entire washing or cleaning composition. Unless explicitly stated otherwise, this also applies to all the quantities stated below.

In an exemplary embodiment, the water-soluble builder block contains at least 2 of components b), c), d) and e) in quantities of greater than 0 wt. %.

With regard to component a), in an exemplary embodiment, from about 15 wt. % to about 25 wt. % of alkali metal carbonate, which may at least in part be replaced by alkali metal hydrogencarbonate, and up to about 5 wt. %, in particular from about 0.5 wt. % to about 2.5 wt. % of citric acid and/or alkali metal citrate are present. In an alternative embodiment, from about 5 wt. % to about 25 wt. %, in particular from about 5 wt. % to about 15 wt. % of citric acid and/or alkali metal citrate and up to about 5 wt. %, in particular from about 1 wt. % to about 5 wt. % of alkali metal carbonate, which may at least in part be replaced by alkali metal hydrogencarbonate, are present as component a). If both alkali metal carbonate and alkali metal hydrogencarbonate are present, an exemplary component a) comprises alkali metal carbonate and alkali metal hydrogencarbonate in a weight ratio of from about 10:1 to about 1:1.

With regard to component b), in an exemplary embodiment, from about 1 wt. % to about 5 wt. % of alkali metal silicate with a modulus in the range of from about 1.8 to about 2.5 are present.

With regard to component c), in an exemplary embodiment, from about 0.05 wt. % to about 1 wt. % of phosphonic acid and/or alkali metal phosphonate are present. Phosphonic acids are here also taken to mean optionally substituted alkylphosphonic acids, which may also comprise two or more phosphonic acid groups ("polyphosphonic acids"). They may be selected from hydroxy- and/or aminoalkylphosphonic acids and/or the alkali metal salts thereof, such as for example dimethylaminomethane diphosphonic acid, 3-aminopropyl-1-hydroxy-1,1-diphosphonic acid, 1-amino-1-phenylmethane diphosphonic acid, 1-hydroxyethane-1,1-diphosphonic acid, aminotris(methylenephosphonic acid), N,N,N',N'-ethylenediamine-tetrakis-(methylenephosphonic acid) and acylated derivatives of phosphorous acid, which may also be used in any desired mixtures.

With regard to component d), in an exemplary embodiment, from about 15 wt. % to about 35 wt. % of alkali metal phosphate, in particular trisodium polyphosphate, are present. "Alkali metal phosphate" is the summary name for the alkali metal (in particular sodium and potassium) salts of the various phosphoric acids, it being possible to distinguish between meta-phosphoric acids (HPO3)n and ortho-phosphoric acid H3PO4 as well as higher molecular weight representatives. The phosphates here combine a number of advantages: they act as alkalinity donors, prevent lime deposits on machine parts or lime incrustation of fabrics and, moreover, contribute to cleaning performance. Sodium dihydrogenphosphate, $NaH_2PO_4$, exists as a dihydrate (density 1.91 $g/cm^3$, melting point 60° C.) and as a monohydrate (density 2.04 $g/cm^3$). Both salts are white powders, very readily soluble in water, which lose their water of crystallization when heated and at 200° C. change into the weakly acidic diphosphate (disodium hydrogendiphosphate, $Na_2H_2P_2O_7$) and at a higher temperature into sodium trimetaphosphate (Na3P3O9) and Maddrell's salt. NaH2PO4 exhibits an acidic reaction; it is obtained when phosphoric acid is adjusted with sodium hydroxide solution to a pH value of 4.5 and the slurry is atomized. Potassium dihydrogenphosphate (primary or monobasic potassium phosphate, potassium diphosphate, KDP), KH2PO4, is a white salt with a density of 2.33 gcm-3, has a melting point of 253° C. (decomposition with formation of (KPO3)x potassium polyphosphate) and is readily soluble in water. Disodium hydrogenphosphate (secondary sodium phosphate), Na2HPO4, is a colorless, very readily water-soluble crystalline salt. It exists in anhydrous form and with 2 mol (density 2.066 gcm-3, water loss at 95° C.), 7 mol (density 1.68 gcm-3, melting point 48° C. with loss of 5H2O) and 12 mol of water (density 1.52 gcm-3, melting point 35° C. with loss of 5H2O), is anhydrous at 100° C. and when heated further changes into the diphosphate Na4P2O7. Disodium hydrogenphosphate is produced by neutralizing phosphoric acid with soda solution using phenolphthalein as indicator. Dipotassium hydrogenphosphate (secondary or dibasic potassium phosphate), K2HPO4, is an amorphous, white salt, which is readily soluble in water. Trisodium phosphate, tertiary sodium phosphate, Na3PO4, are colorless crystals, which have as dodecahydrate a density of 1.62 gcm-3 and a melting point of 73-76° C. (decomposition), as decahydrate (corresponding to 19-20% P2O5) a melting point of 100° C. and in anhydrous form (corresponding to 39-40% P2O5) a density of 2.536 gcm-3. Trisodium phosphate is readily soluble in water with an alkaline reaction and is produced by evaporation of a solution of precisely 1 mol of disodium phosphate and 1 mol of NaOH. Tripotassium phosphate (tertiary or tribasic potassium phosphate), K3PO4, is a white, deliquescent, granular powder with a density of 2.56 gcm-3, has a melting point of 1340° C. and is readily soluble in water with an alkaline reaction. It arises for example when Thomas slag is heated with carbon and potassium sulfate. Despite their relatively high price, the more readily soluble and therefore highly effective potassium phosphates are often selected in the cleaning composition industry over corresponding sodium compounds. Tetrasodium diphosphate (sodium pyrophosphate), Na4P2O7, exists in anhydrous form (density 2.534 gcm-3, melting point 988° C., also stated as 880° C.) and as decahydrate (density 1.815-1.836 gcm-3, melting point 94° C. with water loss). Solid substances comprise colorless crystals which are soluble in water with an alkaline reaction. Na4P2O7 arises on heating disodium phosphate to >200° C. or by reacting phosphoric acid with soda in a stoichiometric ratio and dehydrating the solution by atomization. The decahydrate complexes heavy metal salts and hardness forming substances and therefore reduces the hardness of the water. Potassium diphosphate (potassium pyrophosphate), K4P2O7, exists in the form of the trihydrate and is a colorless, hygroscopic powder with a density of 2.33 gcm-3, which is soluble in water, the pH value of the 1% solution amounting to 10.4 at 25° C. Condensing NaH2PO4 or KH2PO4 gives rise to higher molecular weight sodium and potassium phosphates, in which it is possible to distinguish between cyclic representatives, the sodium or potassium metaphosphates, and chain types, the sodium or potassium polyphosphates. The latter in particular have a plurality of names: fused or thermal phosphates, Graham's salt, Kurrol's salt and Maddrell's salt. All higher sodium and potassium phosphates are jointly designated condensed phosphates. The technically important pentasodium triphosphate, Na5P3O10 (sodium tripolyphosphate), is a non-hygroscopic, white, water-soluble salt, which is anhydrous or crystallized with 6H2O, of the general formula NaO—[P(O)(ONa)—O]n-Na with n=3. At room temperature approx. 17 g, at 60° C. approx. 20 g, at 100° C. around 32 g of the salt containing no water of crystallization dissolve in 100 g of water; after heating the solution for two hours to 100° C., approx. 8% orthophosphate and 15% diphosphate are obtained by hydrolysis. When producing pentasodium triphosphate, phosphoric acid is reacted with soda solution or sodium hydroxide solution in a stoichiometric ratio and the solution is dehydrated by atomization.

As with Graham's salt and sodium diphosphate, pentasodium triphosphate dissolves many insoluble metal compounds (even lime soaps etc.). Pentapotassium triphosphate, K5P3O10 (potassium tripolyphosphate), is commercially available, for example, in the form of a 50 wt. % solution (>23% P2O5, 25% K2O). Potassium polyphosphates are widely used in the washing and cleaning composition industry. Sodium potassium tripolyphosphates also exist, which may likewise be used for the purposes herein. These arise for example if sodium trimetaphosphate is hydrolyzed with KOH:

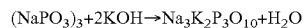

$$(NaPO_3)_3 + 2KOH \rightarrow Na_3K_2P_3O_{10} + H_2O$$

They may be used according to embodiments herein in exactly the same way as sodium tripolyphosphate, potassium tripolyphosphate or mixtures of these two; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate may also be used according to embodiments herein.

With regard to component e), in an exemplary embodiment, from about 1.5 wt. % to about 5 wt. % of polymeric polycarboxylate are present, in particular selected from the polymerization or copolymerization products of acrylic acid, methacrylic acid and/or maleic acid. Among these, the homopolymers of acrylic acid are suitable and, among these in turn, those with an average molar mass in the range from about 5,000 D to about 15,000 D (PA standard) are particularly suitable.

In another embodiment, an exemplary detergent composition comprises one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases: The additional enzyme may be another protease or protease variant. The protease may be of animal, vegetable or microbial origin, including chemically or genetically modified mutants. Microbial origin is preferred. It may be an alkaline protease, such as a serine protease or a metalloprotease. A serine protease may for example be of the S1 family, such as trypsin, or the S8 family such as subtilisin. A metalloproteases protease may for example be a thermolysin from, for example, family M4, M5, M7 or M8.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. In one embodiment, the additional protease may be a subtilase, such as a subtilisin or a variant hereof.

Examples of subtilisins are those derived from *Bacillus* such as subtilisin *lentus, Bacillus lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 (WO 93/18140). Additional serine protease examples are described in WO 98/020115, WO 01/44452, WO 01/58275, WO 01/58276, WO 03/006602 and WO 04/099401. Further examples of subtilase variants may be those having mutations in any of the positions: 3, 4, 9, 15, 27, 36, 68, 76, 87, 95, 96, 97, 98, 99, 100, 101, 102, 103, 104, 106, 118, 120, 123, 128, 129, 130, 160, 167, 170, 194, 195, 199, 205, 217, 218, 222, 232, 235, 236, 245, 248, 252 and 274 using the BPN' numbering. In an exemplary embodiment, the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D, N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering). A further exemplary protease is the alkaline protease from *Bacillus lentus* DSM 5483, as described for example in WO 95/23221, and variants thereof which are described in WO 92/21760, WO 95/23221, EP 1921147 and EP 1921148.

Examples of trypsin-like proteases are trypsin (e.g., of porcine or bovine origin) and the *Fusarium* protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Examples of metalloproteases are the neutral metalloprotease as described in WO 07/044993.

Exemplary commercially available protease enzymes include Alcalase™, Coronase™, Duralase™, Durazym™, Esperase™, Everlase™, Kannase™, Liquanase™, Liquanase Ultra™, Ovozyme™, Polarzyme™, Primase™, Relase™, Savinase™ and Savinase Ultra™, (Novozymes A/S), Axapem™ (Gist-Brocases N.V.), Excellase™, FN2™, FN3™, FN4™, Maxaca™, Maxapem™, Maxatase™, Properase™, Purafast™, Purafect™, Purafect OxP™, Purafect Prime™ and Puramax™ (DuPont/Genencor int.).

Lipases and Cutinases: Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258 068 and EP 305 216, cutinase from *Humicola*, e.g., *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO2007/087508 and WO 2009/109500.

Exemplary commercially available lipase enzymes include Lipolase™, Lipolase Ultra™, and Lipex™; Lecitase™, Lipolex™; Lipoclean™, Lipoprime™ (Novozymes A/S). Other commercially available lipases include Lumafast (Genencor Int Inc); Lipomax (Gist-Brocades/Genencor Int Inc) and *Bacillus* sp lipase from Solvay.

Amylases: Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive, i.e., a separate additive or a combined additive, can be formulated, for example, as a granulate, liquid, slurry, etc. Exemplary detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

In another embodiment, the composition contains from about 5 wt. % to about 50 wt. %, in particular from about 8 to about 30 wt. % of anionic and/or nonionic surfactant, up to about 60 wt. %, in particular from about 5 to about 40 wt. %, of builder substance, and from about 0.2 wt. % to about 2 wt. % of enzyme, selected from proteases, lipases, cutinases, amylases, pullulanases, mannanases, cellulases, oxidases and peroxidases and mixtures thereof.

Organic solvents which may be used in the compositions described herein, in particular if these are in liquid or pasty form, include alcohols with 1 to 4 C atoms, in particular methanol, ethanol, isopropanol and tert.-butanol, diols with 2 to 4 C atoms, in particular ethylene glycol and propylene glycol, and mixtures thereof and the ethers derivable from the stated classes of compounds. Such water-miscible solvents may be present in the washing compositions described herein in quantities of no more than about 30 wt. %, in particular from about 6 wt. % to about 20 wt. %.

In order to establish a desired pH value which is not automatically obtained by mixing the remaining components, the compositions described herein may contain acids which are compatible with the system and are environmentally compatible, in particular citric acid, acetic acid, tartaric acid, malic acid, lactic acid, glycolic acid, succinic acid, glutaric acid and/or adipic acid, as well as mineral acids, in particular sulfuric acid, or bases, in particular ammonium or alkali metal hydroxides. Such pH regulators are present in exemplary compositions in an amount of no more than about 20 wt. %, in particular from about 1.2 wt. % to about 17 wt. %.

Polymers with a soil detachment capacity, which are often known as "soil release" active ingredients or, due to their ability to provide a soil-repelling finish on the treated surface, for example the fiber, as "soil repellents," are for example nonionic or cationic cellulose derivatives. Polymers with a soil detachment capacity, in particular with regard to polyesters, include copolyesters prepared from dicarboxylic acids, for example adipic acid, phthalic acid or terephthalic acid, diols, for example ethylene glycol or propylene glycol, and polydiols, for example polyethylene glycol or polypropylene glycol. Polyesters with a soil detachment capacity which may be used include those compounds which, in formal terms, are obtainable by esterifying two monomer moieties, the first monomer being a dicarboxylic acid HOOC-Ph-COOH and the second monomer a diol HO—(CHR11-)aOH, which may also be present as a polymeric diol H—(O—(CHR11-)a)bOH. Ph here means an o-, m- or p-phenylene residue which may bear 1 to 4 substituents selected from alkyl residues with 1 to 22 C atoms, sulfonic acid groups, carboxyl groups and mixtures thereof, R11 means hydrogen, an alkyl residue with 1 to 22 C atoms and mixtures thereof, a means a number from 2 to 6 and b a number from 1 to 300. The polyesters obtainable therefrom may contain not only monomer diol units —O—(CHR11-)aO— but also polymer diol units —(O—(CHR11-)a)bO—. The molar ratio of monomer diol units to polymer diol units may amount to about 100:1 to about 1:100, in particular from about 10:1 to about 1:10. In the polymer diol units, the degree of polymerization b may be in the range of from about 4 to about 200, in particular from about 12 to about 140. The molecular weight or average molecular weight or the maximum of the molecular weight distribution of suitable polyesters with a soil detachment capacity is in the range of from about 250 to about 100,000, in particular from about 500 to about 50,000. The acid on which the residue Ph is based may be selected from terephthalic acid, isophthalic acid, phthalic acid, trimellitic acid, mellitic acid, the isomers of sulfophthalic acid, sulfoisophthalic acid and sulfoterephthalic acid and mixtures thereof. Where the acid groups thereof are not part of the ester bond in the polymer, they may be present in salt form, in particular as an alkali metal or ammonium salt. Among these, sodium and potassium salts are particularly preferred. If desired, instead of the monomer HOOC-Ph-COOH, the polyester with a soil detachment capacity may contain small proportions, in particular no more than 10 mol % relative to the proportion of Ph with the above-stated meaning, of other acids which comprise at least two carboxyl groups. These include, for example, alkylene and alkenylene dicarboxylic acids such as malonic acid, succinic acid, fumaric acid, maleic acid, glutaric acid, adipic acid, pimelic acid, suberic acid, azelaic acid and sebacic acid. Exemplary diols HO—(CHR11-)aOH include those in which R11 is hydrogen and a is a number from 2 to 6, and those in which a has the value 2 and R11 is selected from hydrogen and alkyl residues with 1 to 10, in particular 1 to 3 C atoms. Among the latter-stated diols, those of the formula HO—CH2-CHR11-OH, in der R11 has the above-stated meaning, are particularly preferred. Examples of diol components are ethylene glycol, 1,2-propylene glycol, 1,3-propylene glycol, 1,4-butanediol, 1,5-pentanediol, 1,6-hexanediol, 1,8-octanediol, 1,2-decanediol, 1,2-dodecanediol and neopentyl glycol. Among the polymeric diols, polyethylene glycol with an average molar mass in the range from 1000 to 6000 is particularly preferred. If desired, these polyesters may also be end group-terminated, with end groups which may be considered being alkyl groups with 1 to 22 C atoms and esters of monocarboxylic acids. The end groups attached via ester bonds may be based on alkyl, alkenyl and aryl monocarboxylic acids with 5 to 32 C atoms, in particular 5 to 18 C atoms. These include valeric acid, caproic acid, enanthic acid, caprylic acid, pelargonic acid, capric acid, undecanoic acid, undecenoic acid, lauric acid, lauroleic acid, tridecanoic acid, myristic acid, myristoleic acid, pentadecanoic acid, palmitic acid, stearic acid, petroselinic acid, petroselaidic acid, oleic acid, linoleic acid, linolaidic acid, linolenic acid, eleostearic acid, arachidic acid, gadoleic acid, arachidonic acid, behenic acid, erucic acid, brassidic acid, clupanodonic acid, lignoceric acid, cerotic acid, melissic acid, benzoic acid, which may bear 1 to 5 substituents having a total of up to 25 C atoms, in particular 1 to 12 C atoms, for example tert.-butylbenzoic acid. The end groups may also be based on hydroxymonocarboxylic acids with 5 to 22 C atoms, which for example include hydroxyvaleric acid, hydroxycaproic acid, ricinoleic acid, the hydrogenation product thereof, hydroxystearic acid, and o-, m- and p-hydroxybenzoic acid. The hydroxymonocarboxylic acids may in turn be joined to one another via their hydroxyl group and their carboxyl group and thus be repeatedly present in an end group. The number of hydroxymonocarboxylic acid units per end group, i.e. their degree of oligomerization, may be in the range from 1 to 50, in particular from 1 to 10. In an exemplary embodiment, polymers of ethylene terephthalate and polyethylene oxide terephthalate, in which the polyethylene glycol units have molar weights of from about 750 to about 5000 and the molar ratio of ethylene terephthalate to polyethylene oxide terephthalate amounts to from about 50:50 to about 90:10, are used alone or in combination with cellulose derivatives.

Dye transfer inhibitors which may be considered for use in compositions according to embodiments herein for washing textiles include in particular polyvinylpyrrolidones, polyvinylimidazoles, polymeric N-oxides such as poly-(vinylpyridine-N-oxide) and copolymers of vinylpyrrolidone with vinylimidazole and optionally further monomers.

The compositions according to embodiments herein for use in washing textile may contain anticrease compositions since textile fabrics, in particular made from rayon, wool, cotton and mixtures thereof, may have a tendency to crease, because the individual fibers are sensitive to being bent, kinked, pressed and squashed transversely of the fiber direction. These include for example synthetic products based on fatty acids, fatty acid esters, fatty acid amides, fatty acid alkylol esters, fatty acid alkylol amides or fatty alcohols, which have generally been reacted with ethylene oxide, or products based on lecithin or modified phosphoric acid esters.

Graying inhibitors have the task of keeping dirt which has been dissolved away from the hard surface and in particular from the textile fiber suspended in the liquor. Water-soluble colloids of a mainly organic nature are suitable for this purpose, for example starch, size, gelatin, salts of ether carboxylic acids or ether sulfonic acids of starch or cellulose or salts of acidic sulfuric acid esters of cellulose or starch. Water-soluble polyamides containing acidic groups are also suitable for this purpose. Derivatives of starch other than those stated above, for example aldehyde starches, may further be used. Cellulose ethers, such as carboxymethylcellulose (Na salt), methylcellulose, hydroxyalkylcellulose and mixed ethers, such as methylhydroxyethylcellulose, methylhydroxypropylcellulose, methylcarboxymethylcellulose and mixtures thereof, may be used, for example in quantities of from about 0.1 to about 5 wt. % relative to the compositions.

The washing compositions may contain optical brighteners, among these in particular derivatives of diaminostilbene disulfonic acid or the alkali metal salts thereof. Suitable compounds are, for example, salts of 4,4'-bis(2-anilino-4-morpholino-1,3,5-triazinyl-6-amino)stilbene 2,2'-disulfonic acid or compounds of similar structure which, instead of the morpholino group, bear a diethanolamino group, a methylamino group, an anilino group or a 2-methoxyethylamino group. Brighteners of the substituted diphenylstyryl type may furthermore be present, for example the alkali metal salts of 4,4'-bis(2-sulfostyryl)diphenyl, 4,4'-bis(4-chloro-3-sulfostyryl)diphenyl, or 4-(4-chlorostyryl)-4'-(2-sulfostyryl) diphenyl. Mixtures of the above-stated optical brighteners may also be used.

Especially for use in machine washing or cleaning methods, it may be advantageous to add conventional foam inhibitors to the compositions. Suitable foam inhibitors are, for example, soaps of natural or synthetic origin, which comprise an elevated proportion of C18-C24 fatty acids. Suitable non-surfactant foam inhibitors are, for example, organopolysiloxanes and mixtures thereof with microfine, optionally silanized silica as well as paraffins, waxes, microcrystalline waxes and mixtures thereof with silanized silica or bis-fatty acid alkylenediamides. Mixtures of different foam inhibitors are also advantageously used, for example mixtures of silicones, paraffins or waxes. The foam inhibitors, in particular foam inhibitors containing silicone and/or paraffin, may be bound to a granular carrier substance which is soluble or dispersible in water. Mixtures of paraffins and bistearylethylenediamide are particularly suitable here.

Active ingredients for avoiding tarnishing of silver objects or "silver corrosion inhibitors" may moreover be used in compositions according to embodiments herein. Exemplary silver anticorrosion compositions are organic disulfides, dihydric phenols, trihydric phenols, optionally alkyl- or aminoalkyl-substituted triazoles such as benzotriazole and cobalt, manganese, titanium, zirconium, hafnium, vanadium or cerium salts and/or complexes, in which the stated metals are present in one of the oxidation states II, III, IV, V or VI.

The protease variant may assume the form of powder or granules, which may also optionally be coated and/or colored and may contain conventional carrier materials and/or granulation auxiliaries. In the case of use in granule form, the granules may if desired also contain further active substances.

In another exemplary embodiment, the detergent composition is a liquid or a solid, such as a solid which is a powder or is in granular form or is a tablet. In another embodiment, the composition is a machine dishwashing composition in particular for automatic dishwashing which is in tablet form.

The production of solid compositions according to embodiments herein is unproblematic and may proceed in a manner known in principle, for example by spray drying or granulation, with any peroxy compound and bleach-boosting active ingredient optionally being added subsequently. Compositions described herein with an elevated bulk density, in particular in the range from about 650 g/l to about 950 g/l, may be produced by a method comprising an extrusion step. Washing or cleaning compositions or disinfectants according to embodiments herein in the form of aqueous solutions or solutions containing other conventional solvents are particularly advantageously produced by simply mixing the ingredients, which may be introduced into an automatic mixer without solvent or as a solution.

Formulation of Detergent Products

The detergent composition of embodiments herein may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multiple compartments. It can be of any form, shape and material which is suitable for hold the composition, e.g., without allowing the release of the composition to release of the composition from the pouch prior to water contact. The pouch is made from water soluble film which encloses an inner volume. Said inner volume can be divided into compartments of the pouch. Exemplary films are polymeric materials, such as polymers which are formed into a film or sheet. Exemplary polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, such as polyvinyl alcohol copolymers and hydroxypropyl methyl cellulose (HPMC). In an exemplary embodiment, the level of polymer in the film for example PVA is at least about 60%. Exemplary average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1)

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951.

WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,

WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792,

WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636,

Methods and Uses

The present disclosure is also directed to methods for using the detergent compositions described herein in laundry of textile and fabrics, such as house hold laundry washing and industrial laundry washing.

The disclosure is also directed to methods for using the detergent compositions described herein in hard surface cleaning such as automated Dish Washing (ADW), car wash and cleaning of industrial surfaces.

The protease variants described herein may be added to and thus become a component of the detergent compositions according to embodiments herein. Thus one embodiment relates to the use of a detergent composition comprising a protease variant wherein said variant comprises a substitution of one or more amino acids in the loop corresponding to positions 171, 173, 175 or 179 of SEQ ID NO: 3, wherein the variant has at least 70% identity to SEQ ID NO: 3 in a cleaning process such as laundry and/or hard surface cleaning e.g., dish wash. Another aspect relates to the use of a detergent composition comprising a variant wherein said variant comprises one or more of the following substitutions S171 {W, K, E}, S173 {P}, S175 {A, V, P} or G179 {C, V, Q, S, T, E, H, K, M, N} of SEQ ID NO: 3, wherein the variant has a sequence identity to SEQ ID NO: 3 of at least 70% and less than 100% and the variant has protease activity.

One embodiment relates to the use of a protease variant, comprising one or more of the following substitutions S171 {W, K, E}, S173 {P}, S175 {A, V, P}, G179 {C, V, Q, S, T, E, H, K, M, N} of SEQ ID NO: 3, wherein the variant has at least 70% identity to SEQ ID NO: 3 in a cleaning process such as laundry and/or hard surface cleaning and wherein the variant has increased detergent stability relative to the parent or relative to a protease parent having the identical amino acid sequence of said variant but not having the substitutions at one or more of said positions when tested in the Example 2, as described under "Material and Methods".

Additionally, any of the protease variants described above wherein the protease variants are comprised in detergent compositions according to embodiments herein may also contain a substitution at position F180Y.

An exemplary detergent composition may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

An exemplary embodiment of the composition includes a detergent additive comprising a polypeptide as described herein.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, a process for laundering of fabrics and/or garments is provided where the process comprises treating fabrics with a washing solution containing a detergent composition, and at least one protease variant as described herein. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process may be conventional washable laundry, for example household laundry. In an exemplary embodiment, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabbit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Embodiments herein further concern the use of detergent compositions described herein in a proteinaceous stain removing processes. The proteinaceous stains may be stains such as food stains, e.g., baby food, sebum, cocoa, egg, blood, milk, ink, grass, or a combination hereof.

Typical detergent compositions include various components in addition to the enzymes, these components have different effects, some components like the surfactants lower the surface tension in the detergent, which allows the stain being cleaned to be lifted and dispersed and then washed away, other components like bleach systems remove discolor often by oxidation and many bleaches also have strong bactericidal properties, and are used for disinfecting and sterilizing. Yet other components like builder and chelator softens, e.g., the wash water by removing the metal ions form the liquid.

In a particular embodiment, a composition comprising a protease variant as described herein, wherein said enzyme composition further comprises at least one or more of the following: a surfactant, a builder, a chelator or chelating agent, bleach system or bleach component, is provided for use in laundry or dish wash.

In an exemplary embodiment, the amount of a surfactant, a builder, a chelator or chelating agent, bleach system and/or bleach component are reduced compared to amount of surfactant, builder, chelator or chelating agent, bleach system and/or bleach component used without the added protease variant described herein. The at least one component which is a surfactant, a builder, a chelator or chelating agent, bleach system and/or bleach component may be present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, or such as 50% less, than the amount of the component in the system without the addition of protease variants described herein, such as a conventional amount of such component. In one aspect, a protease variant described herein is used in detergent compositions wherein said composition is free of at least one component which is a surfactant, a builder, a chelator or chelating agent, bleach system or bleach component and/or polymer.

Washing Method

Exemplary detergent compositions described herein are ideally suited for use in laundry applications. Accordingly, a method for laundering a fabric is provided. The method comprises the steps of contacting a fabric to be laundered with a cleaning laundry solution comprising the detergent composition described herein. The fabric may comprise any fabric capable of being laundered in normal consumer use conditions. An exemplary solution has a pH of from about 5.5 to about 11.5. The compositions may be employed at concentrations of from about 100 ppm, such as from about 500 ppm, to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or from about 6 to about 10.5, about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, about 8 to about 11, about 8 to about 10, about 8 to about 9, about 9 to about 11, about 9 to about 10, or about 10 to about 11, for example, from about 5.5 to about 11.5.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, or about 30° dH. Under typical European wash conditions, the degree of hardness is about 16° dH, under typical US wash conditions, the degree of hardness is about 6° dH, and under typical Asian wash conditions, the degree of hardness is about 3° dH.

Exemplary embodiments relate to a method of cleaning a fabric, a dishware or hard surface with a detergent composition comprising a protease variant described above.

An exemplary embodiment concerns a method of cleaning, said method comprising the steps of: contacting an object with a cleaning composition comprising a protease variant under conditions suitable for cleaning said object. In an exemplary embodiment the cleaning composition is a detergent composition and the process is a laundry or a dish wash process.

Still another embodiment relates to a method for removing stains from fabric which comprises contacting said a fabric with a composition comprising a protease as described above under conditions suitable for cleaning said object.

In another embodiment, the compositions for use in the methods above further comprises at least one additional enzyme as set forth in the "other enzymes" section above, such as an enzyme selected from the group of hydrolases such as proteases, lipases and cutinases, carbohydrases such as amylases, cellulases, hemicellulases, xylanases, and pectinase or a combination hereof. In yet another embodiment, the compositions for use in the methods above comprise a reduced amount of at least one or more of the following components a surfactant, a builder, a chelator or chelating agent, bleach system or bleach component or a polymer.

Also contemplated are compositions and methods of treating fabrics (e.g., to desize a textile) using one or more of the protease described herein. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

In one embodiment, the protease variant is applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The protease variant can be applied to remove these sizing protein or protein derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme.

All issues, subject matter and embodiments which are disclosed for protease variants in this application are also applicable for methods and uses described herein. Therefore, it is explicitly referred to said disclosure for the methods and uses described herein as well.

Embodiments herein are further described by the following examples that should not be construed as limiting the scope of the composition and methods.

EXAMPLES

Materials and Methods
Automatic Mechanical Stress Assay (AMSA) for Laundry
In order to assess the wash performance in laundry washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO02/42740 especially the paragraph "Special method embodiments" at page 23-24.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Colour measurements are made with a professional flat-bed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int = \sqrt{r^2 + g^2 + b^2}.$$

TABLE 1

Composition of model detergents and test materials
Model detergent and test materials were as follows:

| | |
|---|---|
| Laundry liquid model detergent | 0.3 to 0.5% xanthan gum, 0.2 to 0.4% antifoaming agent, 6 to 7% glycerol, 0.3 to 0.5% ethanol, 4 to 7% FAEOS (fatty alcohol ether sulfate), 24 to 28% nonionic surfactants, 1% boric acid, 1 to 2% sodium citrate (dihydrate), 2 to 4% soda, 14 to 16% coconut fatty acid, 0.5% HEDP (1-hydroxyethane-(1,1-diphosphonic acid)), 0 to 0.4% PVP (polyvinylpyrrolidone), 0 to 0.05% optical brighteners, 0 to 0.001% dye, remainder deionized water. |
| Test material | PC-03 (Chocolate-milk/ink on cotton/polyester) C-05 (Blood/milk/ink on cotton) |

General Molecular Biology Methods:
Unless otherwise mentioned the DNA manipulations and transformations were performed using standard methods of molecular biology (Sambrook et al. (1989); Ausubel et al. (1995); Harwood and Cutting (1990).

Protease Activity Assays:

1) Suc-AAPF-pNA Activity Assay:

The proteolytic activity can be determined by a method employing the Suc-AAPF-PNA substrate. Suc-AAPF-PNA is an abbreviation for N-Succinyl-Alanine-Alanine-Proline-Phenylalanine-p-Nitroanilide, and it is a blocked peptide which can be cleaved by endo-proteases. Following cleavage a free PNA molecule is liberated and it has a yellow colour and thus can be measured by visible spectrophotometry at wavelength 405 nm. The Suc-AAPF-PNA substrate is manufactured by Bachem (cat. no. L1400, dissolved in DMSO).

The protease sample to be analyzed was diluted in residual activity buffer (100 mM Tris pH8.6). The assay was performed by transferring 60 µl of diluted enzyme samples to 96 well microtiter plate and adding 140 µl substrate working solution (0.72 mg/ml in 100 mM Tris pH8.6). The solution was mixed at room temperature and absorption is measured every 20 sec. over 5 minutes at OD 405 nm.

The slope (absorbance per minute) of the time dependent absorption-curve is directly proportional to the specific activity (activity per mg enzyme) of the protease in question under the given set of conditions. The protease sample should be diluted to a level where the slope is linear.

Example 1: Preparation and Testing of Protease Variants

Preparation and Expression of Variants

Site-directed variants were constructed of the TY145 protease (SEQ ID NO: 3) comprising specific insertions/deletions/substitutions in the 170 to 180 region on the N-terminal side as described herein. The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence. Mutagenic oligos were synthesized corresponding to the DNA sequence flanking the desired site(s) of mutation, separated by the DNA base pairs defining the insertions/deletions/substitutions. In this manner, the variants listed in table 2a below were constructed and produced.

Fermentation of Variants

Fermentation may be performed by methods well known in the art or as follows. A B. subtilis strain harboring the relevant expression plasmid was streaked on a LB-agar plate with a relevant antibiotic (6 µg/ml chloramphenicol), and grown overnight at 37° C.

The colonies were transferred to 100 ml PS-1 media supplemented with the relevant antibiotic in a 500 ml shaking flask containing a rich media (e.g., PS-1: 100 g/L Sucrose (Danisco cat. no. 109-0429), 40 g/L crust soy (soy bean flour), 10 g/L Na2HPO4.12H2O (Merck cat. no. 6579), 0.1 ml/L Pluronic PE 6100 (BASF 102-3098)). Cultivation typically takes 4 days at 30° C. shaking with 220 rpm. Cells and other undissolved material were removed from the fermentation broth by centrifugation at 4500 rpm for 20-25 minutes. Afterwards the supernatant was filtered to obtain a clear solution.

Example 2

In this example the above-described PNA-Suc-AAPF assay is used to determine the residual protease activity after incubation in the presence of liquid detergent. In general the residual protease activity was determined after incubation in liquid detergent (final concentration of 90%) at the indicated temperatures and incubation times and the activity is then compared to the activity of a unstressed incubated at 4° C. For the determination of protease stability in detergent the enzymes to be tested were adjusted to a concentration of 0.15 mg/ml of enzyme protein by dilution in enzyme dilution buffer (100 mM Tris pH 8.6, 0.0225% (w/V) Brij-35, 2 mM CaCl2). 30 µl of the protease solution and 270 µl liquid detergent (Model liquid detergent) were transferred to a 96 well microtiter plate (Nunc 96U PP) in 4 replicates. One small magnet (5×2 mm) was placed in each well, and the blend was mixed for 30 minutes at room temperature on a magnetic stirrer. After mixing 20 µl is transferred to new 96 well microtiter plate and incubated at 4° C. for 24 hours (unstressed sample). Heat seal with alu-foil carefully microtiter plate and incubate at indicated temperature for 24 hours (stressed samples). After incubation, the samples on the plates were analyzed for protease activity as described in the PNA-Suc-AAPF Assay for determination of residual protease activity. It should be noted, that in order to reduce interference from other detergent ingredients than the enzyme on the assay, both unstressed and stressed samples were diluted to the same protein concentration.

After incubation, withdraw 20 µl of stressed samples and add 150 µl residual activity buffer (100 mM Tris pH8.6), and mix using magnetic stirrer for 5 minutes. Transfer 60 µl of diluted sample to new 96 well microtiter plate. Before use prepare PNA-Suc-AAPF substrate working solution in residual activity buffer (0.72 mg/ml in 100 mM Tris pH8.6). Add 140 µl substrate working solution to diluted sample, mix and measure immediately absorbance at 405 nm for 5-10 minutes every 20 seconds at room temperature. Use Vmax only from linear range of kinetic curves. Repeat residual activity measurement for unstressed sample by adding 150 µl residual activity buffer (100 mM Tris pH8.6) to microtiter plate with 20 µl unstressed sample (incubated at 4° C.), and mix using magnetic stirrer for 5 minutes. Transfer 60 µl of diluted sample to new 96 well microtiter plate. Add 140 µl substrate working solution to diluted sample, mix and measure immediately absorbance at 405 nm for 5-10 minutes every 20 seconds at room temperature. Use Vmax only from linear range of kinetic curves.

It was ensured in all experiments that the reference protease was included at least once on all test microtiter plates.

The residual activity (% RA) was calculated as % RA=100*Vmax (stressed sample)/Vmax (unstressed sample).

The half-life (T½(h)) is calculated: T½ (hours)=T(hours) *LN(0.5)/LN(% RA/100) with T being incubation time (hours) and % RA is residual activity.

TABLE 3a stability of variants measured at 35° C.

| Mutations | Half-life T½ (hours) (incubation at 35° C. for 24 h in 90% detergent) |
|---|---|
| TY-145 (SEQ ID NO 3) | 18 |
| G179C | 36 |
| G179V | 56 |
| G179Q | 65 |
| G179S | 29 |

TABLE 3a-continued stability of variants measured at 35° C.

| Mutations | Half-life T½ (hours) (incubation at 35° C. for 24 h in 90% detergent) |
|---|---|
| G179Y | 67 |
| G179T | 31 |
| G179E | 28 |
| G179H | 79 |
| G179K | 47 |
| G179M | 29 |
| G179A | 82 |
| G179N | 37 |
| S171W | 28 |
| S171K | 23 |
| S171E | 23 |
| S175A | 44 |
| S175V | 30 |
| S175P | 108 |

TABLE 3b stability of variants measured at 35° C.

| Mutations | Half-life T½ (hours) (incubation at 35° C. for 24 h in 90% detergent) |
|---|---|
| TY-145 (SEQ ID NO 3) | 18 |
| I121V S175P | 96 |
| S175A G179S | 78 |
| L81V S175A | 90 |
| A102T S175A | 86 |
| S144R G179Q | 96 |
| S144R S171N | 96 |
| S144Q F180Y | 75 |
| S144R F180Y | 70 |
| S171N L-97P | 40 |
| G179S F180Y G183A A187V | 95 |

TABLE 4a

Stability of variants measured at 42° C.

| Mutations | Half-life T½ (hours) (incubation at 42° C. for 24 h in 90% detergent) |
|---|---|
| TY-145 (SEQ ID NO 3) | 0 |
| S173P | 96 |
| S171N S175P | 10 |
| I121V S175P | 7 |
| L81V S175P | 6 |
| A102T S175P | 6 |
| I137E S175P | 7 |
| I121V S175A | 3 |
| L81F S175A | 3 |
| I137E S175A | 4 |
| S144Q S175P | 6 |
| S144Q S175A | 3 |
| I121T S175P | 8 |

TABLE 4b

Stability of variants measured at 42° C.

| Mutations | Half-life T½ (hours) (incubation at 42° C. for 24 h in 90% detergent) |
|---|---|
| TY-145 (SEQ ID NO 3) | 0 |
| S173Y G174S S175A F180Y | 96 |
| I137E S173Y G174S S175A F180Y | 11 |
| S144Q S173Y G174S S175A F180Y | 9 |
| S173Y G174S S175A F180Y S274I | 10 |
| S173Y G174S S175A F180Y V286Q | 10 |
| T40D S173Y G174S S175A F180Y | 9 |
| S173P G174K S175P N176G T177S F180Y | 30 |
| D155N G159S S173Y G174S S175A F180Y | 6 |
| I121V S173P G174K S175P N176G T177S F180Y | 52 |
| L81V S173P G174K S175P N176G T177S F180Y | 41 |
| A102T S173P G174K S175P N176G T177S F180Y | 37 |
| S173P G174K S175P N176G T177S F180Y T241P | 48 |
| I137E S173P G174K S175P N176G T177S F180Y | 41 |
| S144Q S173P G174K S175P N176G T177S F180Y | 41 |
| Q70N S173P G174K S175P N176G T177S F180Y | 59 |
| S173P G174K S175P N176G T177S F180Y V286Q | 45 |
| T40D S173P G174K S175P N176G T177S F180Y | 32 |
| S171N S173P G174K S175P N176G T177S F180Y | 52 |
| S173P G174K S175P N176G T177S F180Y S274I | 44 |

TABLE 5a

Stability of variants measured at 47° C.

| Mutations | Half-life T½ (hours) (incubation at 47° C. for 24 h in 90% detergent) |
|---|---|
| TY-145 (SEQ ID NO 3) | 0 |
| S173P | 26 |
| S171N S175P | 6 |
| I121V S175P | 6 |
| L81V S175P | 6 |
| A102T S175P | 6 |
| I137E S175P | 6 |
| I121V S175A | 6 |
| L81F S175A | 6 |
| I137E S175A | 6 |
| S144Q S175P | 6 |
| S144Q S175A | 6 |
| I121T S175P | 6 |
| S173P S274I | 29 |
| I137M S173P | 30 |
| S171N S173P | 38 |
| L81F S173P | 28 |
| L81H S173P | 27 |
| A102T S173P | 26 |
| S144Q S173P | 29 |
| I137E S173P | 35 |
| S173P T241P | 32 |
| S173P S175A | 34 |
| L81G S173P | 39 |

TABLE 5b

Stability of variants measured at 47° C.

| Mutations | Half-life T½ (hours) (incubation at 47° C. for 24 h in 90% detergent) |
|---|---|
| TY-145 (SEQ ID NO 3) | 0 |
| S173P S175P F180Y | 96 |
| T74M I137E S173P | 26 |
| T79I I137E S173P | 27 |

TABLE 5b-continued

Stability of variants measured at 47° C.

| Mutations | Half-life T½ (hours) (incubation at 47° C. for 24 h in 90% detergent) |
|---|---|
| L34I I137E S173P | 36 |
| Y39D I137E S173P | 39 |
| T40P I137E S173P | 46 |
| I137E S173P I247M | 41 |
| I137E S173P H256F | 31 |
| S173Y G174S S175A F180Y | 22 |
| I137E S173Y S175A F180Y | 6 |
| S173Y G174S A175P F180Y | 6 |
| I137E S173P S175P F180Y | 96 |
| V162R S173P S175P F180Y | 96 |
| S173P S175P F180Y S274I | 96 |
| S173P G174T S175V T177S F180Y | 39 |
| S173P G174T S175V T177S F180Y | 39 |
| S173Y G174S S175A F180Y T241P | 6 |
| I137E S173Y G174S S175A F180Y | 6 |
| S144Q S173Y G174S S175A F180Y | 6 |
| Q70N S173Y G174S S175A F180Y | 6 |
| S173Y G174S S175A F180Y S274I | 6 |
| S173Y G174S S175A F180Y V286Q | 6 |
| T40D S173Y G174S S175A F180Y | 6 |
| V162R S173Y G174S S175A F180Y | 6 |
| V162R S173Y G174S S175A F180Y | 6 |
| I121V S173Y G174S S175A F180Y | 6 |
| L81V S173Y G174S S175A F180Y | 6 |
| A102T S173Y G174S S175A F180Y | 6 |
| S173P G174T S175A T177S F180Y | 39 |
| I137E S173P S175V T177S F180Y | 34 |
| S171N S173Y G174S S175A F180Y | 6 |
| I137E S173Y G174S A175P F180Y | 7 |
| S173P G174T V175P T177S F180Y | 61 |
| S173P G174K S175P N176G T177S F180Y | 6 |
| V162R S173P G174T S175V T177S F180Y | 62 |
| V162R S173P G174T S175V T177S F180Y | 74 |
| I121V S173P G174T S175V T177S F180Y | 49 |
| L81V S173P G174T S175V T177S F180Y | 41 |
| A102T S173P G174T S175V T177S F180Y | 42 |
| S173P G174T S175V T177S F180Y T241P | 61 |
| I137E S173P G174T S175V T177S F180Y | 86 |
| I137E S173P G174T S175V T177S F180Y | 86 |
| I137E S173P G174T S175V T177S F180Y | 65 |
| S144Q S173P G174T S175V T177S F180Y | 65 |
| Q70N S173P G174T S175V T177S F180Y | 80 |
| S173P G174T S175V T177S F180Y S274I | 56 |
| S173P G174T S175V T177S F180Y V286Q | 56 |
| T40D S173P G174T S175V T177S F180Y | 37 |
| S171N S173P G174T S175V T177S F180Y | 58 |
| I121V I137E S173Y G174S S175A F180Y | 6 |
| L81V I137E S173Y G174S S175A F180Y | 6 |
| L81V I137E S173Y G174S S175A F180Y | 6 |
| I137E S173Y G174S S175A F180Y T241P | 6 |
| Q70N I137E S173Y G174S S175A F180Y | 6 |
| I137E S173Y G174S S175A F180Y S274I | 6 |
| I137E S173Y G174S S175A F180Y T297P | 8 |
| G132I S173P G174T S175V T177S F180Y | 45 |
| S173P G174T S175V T177S F180Y T297P | 72 |
| I137E S144Q S173Y G174S S175A F180Y | 6 |
| T40L I137E S173Y G174S S175A F180Y | 6 |
| I137E S173P S175P N176G T177S F180Y | 6 |
| S173P G174K S175A N176G T177S F180Y | 6 |
| I137E S173Y G174S S175A F180Y V286Q | 6 |
| I137E S173P G174T V175P T177S F180Y | 88 |
| D155N G159S S173P G174T S175V T177S F180Y | 17 |
| V162R S173P G174K S175P N176G T177S F180Y | 11 |
| I121V S173P G174K S175P N176G T177S F180Y | 8 |
| L81V S173P G174K S175P N176G T177S F180Y | 7 |
| A102T S173P G174K S175P N176G T177S F180Y | 7 |
| S173P G174K S175P N176G T177S F180Y T241P | 9 |
| I137E S173P G174K S175P N176G T177S F180Y | 9 |
| S144Q S173P G174K S175P N176G T177S F180Y | 7 |
| Q70N S173P G174K S175P N176G T177S F180Y | 8 |
| S173P G174K S175P N176G T177S F180Y V286Q | 9 |
| T40D S173P G174K S175P N176G T177S F180Y | 7 |
| S171N S173P G174K S175P N176G T177S F180Y | 9 |

TABLE 5b-continued

Stability of variants measured at 47° C.

| Mutations | Half-life T½ (hours) (incubation at 47° C. for 24 h in 90% detergent) |
|---|---|
| I121V I137E S173P G174T S175V T177S F180Y | 73 |
| I137E S173P G174T S175V T177S F180Y T241P | 90 |
| I137E S173P G174T S175V T177S F180Y V286Q | 75 |
| I137E S173P G174T S175V T177S F180Y T297P | 96 |
| I137E S171N S173P G174T S175V T177S F180Y | 78 |
| I137E S171N S173P G174T S175V T177S F180Y | 69 |
| I137E S173P G174K S175A N176G T177S F180Y | 6 |
| G132I S173P G174K S175P N176G T177S F180Y | 6 |
| S173P G174K S175P N176G T177S F180Y T297P | 16 |
| I137E S173P G174T S175V T177S F180Y S274I | 64 |
| I137E S144Q S173P G174T S175V T177S F180Y | 56 |
| S173P G174K S175P N176G T177S F180Y S274I | 7 |
| I121V I137E S173P G174K S175P N176G T177S F180Y | 13 |
| Q70N I137E S173P G174K S175P N176G T177S F180Y | 13 |
| I137E S173P G174K S175P N176G T177S F180Y S274I | 12 |
| I137E S173P G174K S175P N176G T177S F180Y V286Q | 12 |
| I137E S173P G174K S175P N176G T177S F180Y T297P | 23 |
| I137E S171N S173P G174K S175P N176G T177S F180Y | 15 |
| I137E S144Q S173P G174K S175P N176G T177S F180Y | 11 |
| V162R S171N S173P G174K S175P N176G T177S F180Y | 16 |
| I137E S171N S173P G174K S175P N176G T177S F180Y T241P | 22 |
| I137E S171N S173P G174K S175P N176G T177S F180Y T297P | 41 |

TABLE 6

Stability of variants measured at 52° C.

| Mutations | Half-life T½ (hours) (incubation at 52° C. for 24 h in 90% detergent) |
|---|---|
| TY-145 (SEQ ID NO: 3) | 0 |
| I137E S173P | 6 |
| S173P S175P F180Y | 27 |
| T40P I137E S173P | 7 |
| I137E S173P S175P F180Y | 39 |
| V162R S173P S175P F180Y | 45 |
| S173P S175P F180Y S274I | 29 |
| S173P S175P F180Y T297P | 31 |
| S173P S175P F180Y V286Q | 30 |
| S173P G174T S175V T177S F180Y | 11 |
| V162R S173P G174T S175V T177S F180Y | 16 |
| I137E S173P G174T S175V T177S F180Y | 15 |
| Q70N S173P G174T S175V T177S F180Y | 16 |
| S173P G174T S175V T177S F180Y V286Q | 14 |
| S171N S173P G174T S175V T177S F180Y | 15 |
| I137E S173P G174T S175A T177S F180Y | 14 |
| S173P G174T S175V T177S F180Y T297P | 20 |
| I137E S173P G174T V175P T177S F180Y | 37 |
| L81V I137E S173P G174T S175V T177S F180Y | 17 |
| Q70N I137E S173P G174T S175V T177S F180Y | 26 |
| I137E S173P G174T S175V T177S F180Y V286Q | 16 |
| I137E S171N S173P G174T S175V T177S F180Y | 23 |
| I137E S144Q S173P G174T S175V T177S F180Y | 15 |

TABLE 6-continued

Stability of variants measured at 52° C.

| Mutations | Half-life T½ (hours) (incubation at 52° C. for 24 h in 90% detergent) |
|---|---|
| I137E S173P G174T V175P T177S F180Y T297P | >96 |

Example 3

The wash performance of protease variants were tested using a liquid detergent on 3 different technical stains using the Automatic Mechanical Stress Assay.

The experiments were conducted as described in the AMSA for laundry method using a single cycle wash procedure, with the detergent composition and swatches described in table 1 and the experimental conditions as specified in table 7 below.

TABLE 7

Experimental conditions for AMSA for tables 7a to 7f

| Test solution | 4.66 g/L liquid model detergent |
|---|---|
| Test solution volume | 160 micro L |
| pH | As is |
| Wash time | 20 minutes |
| Temperature | 20° C. |
| Water hardness | 16° dH |
| Protease concentration | 0 (blank), 10 nM or 30 nM |
| Swatch | PC-03, C-05 |

Water hardness was adjusted to 16° dH by addition of CaCl2, MgCl2, and NaHCO3

(Ca2+:Mg2+:CO32−)=5:1:6 for PC-03 and 5:1:11 for C-05 to the test system. After washing the textiles were flushed in tap water and dried.

TABLE 7a

Wash performance of single and double protease variants on a Chocolate, Milk, Soot stain, reference enzyme is TY-145 (SEQ ID NO: 3)

| Mutations | Wash performance relative to SEQ ID NO: 3, at 20° C. on PC-03 |
|---|---|
| G179S | 96 |
| S173P | 108 |
| I121V S175A | 106 |
| L81V S175A | 97 |
| S144Q S175P | 112 |
| S144Q S175A | 97 |
| S173P S274I | 102 |
| L81F S173P | 103 |
| S144Q S173P | 101 |
| I137E S173P | 97 |
| S173P T241P | 111 |
| S173P S175A | 106 |
| I121V S144Q | 95 |

TABLE 7b

Wash performance of protease variants on a Chocolate, Milk, Soot stain, reference enzyme is TY-145 (SEQ ID NO 3)

| Mutations | Wash performance relative to SEQ ID NO: 3, at 20° C. on PC-03 |
|---|---|
| S173P S175P F180Y | 91 |
| S173Y G174S S175A F180Y | 101 |
| S173P G174T S175V T177S F180Y | 98 |
| I137E S173Y G174S S175A F180Y | 108 |
| S144Q S173Y G174S S175A F180Y | 101 |
| S173Y G174S S175A F180Y S274I | 117 |
| S173Y G174S S175A F180Y V286Q | 94 |
| V162R S173Y G174S S175A F180Y | 121 |
| I121V S173Y G174S S175A F180Y | 110 |
| S173P G174T S175A T177S F180Y | 106 |
| S173P G174K S175P N176G T177S F180Y | 98 |
| D155N G159S S173Y G174S S175A F180Y | 118 |
| V162R S173P G174T S175V T177S F180Y | 127 |
| V162R S173P G174T S175V T177S F180Y | 123 |
| I121V S173P G174T S175V T177S F180Y | 99 |
| L81V S173P G174T S175V T177S F180Y | 98 |
| I137E S173P G174T S175V T177S F180Y | 116 |
| I137E S173P G174T S175V T177S F180Y | 108 |
| S173P G174T S175V T177S F180Y S274I | 92 |
| S173P G174T S175V T177S F180Y V286Q | 94 |
| I137E S173P G174T S175A T177S F180Y | 91 |
| S173P G174T S175V T177S F180Y T297P | 94 |
| S173P G174K S175A N176G T177S F180Y | 107 |
| D155N G159S S173P G174T S175V T177S F180Y | 116 |
| V162R S173P G174K S175P N176G T177S F180Y | 135 |
| I121V S173P G174K S175P N176G T177S F180Y | 117 |
| L81V S173P G174K S175P N176G T177S F180Y | 104 |
| A102T S173P G174K S175P N176G T177S F180Y | 110 |
| S173P G174K S175P N176G T177S F180Y T241P | 94 |
| I137E S173P G174K S175P N176G T177S F180Y | 122 |
| S144Q S173P G174K S175P N176G T177S F180Y | 107 |
| S173P G174K S175P N176G T177S F180Y V286Q | 112 |
| S171N S173P G174K S175P N176G T177S F180Y | 125 |
| I137E S173P G174T S175V T177S F180Y V286Q | 100 |
| I137E S173P G174K S175A N176G T177S F180Y | 106 |
| G132I S173P G174K S175P N176G T177S F180Y | 92 |
| S173P G174K S175P N176G T177S F180Y T297P | 117 |
| D155N G159S S173P G174K S175P N176G T177S F180Y | 99 |
| S173P G174K S175P N176G T177S F180Y S274I | 125 |
| I121V I137E S173P G174K S175P N176G T177S F180Y | 189 |
| I137E S173P G174K S175P N176G T177S F180Y S274I | 97 |
| I137E S173P G174K S175P N176G T177S F180Y V286Q | 96 |
| I137E S173P G174K S175P N176G T177S F180Y T297P | 128 |
| I137E S171N S173P G174K S175P N176G T177S F180Y | 121 |

TABLE 7c

Wash performance of single and double protease variants on a Blood, Milk, Ink stain, reference enzyme is TY-145 (SEQ ID NO: 3)

| Mutations | Wash performance relative to SEQ ID NO: 3, at 20° C. on C-05 |
|---|---|
| S173P | 110 |
| I121V S175P | 113 |
| L81V S175P | 105 |
| A102T S175P | 100 |
| S175A G179S | 95 |
| I121V S175A | 111 |
| L81V S175A | 101 |
| I137E S175A | 95 |
| S144Q S175P | 116 |
| S144Q S175A | 104 |
| I121T S175P | 98 |
| S144R S171N | 103 |
| S173P S274I | 96 |
| I137M S173P | 105 |
| S171N S173P | 115 |
| L81F S173P | 111 |
| L81H S173P | 103 |
| A102T S173P | 117 |
| S144Q S173P | 108 |
| I137E S173P | 120 |
| S173P T241P | 129 |
| S173P S175A | 100 |

TABLE 7d

Wash performance of protease variants on a Blood, Milk, Ink stain, reference enzyme is TY-145 (SEQ ID NO: 3)

| Mutations | Wash performance relative to SEQ ID NO: 3, at 20° C. on C-05 |
|---|---|
| S173P S175P F180Y | 98 |
| S173Y G174S S175A F180Y | 120 |
| I137E S173Y S175A F180Y | 103 |
| S173P G174T S175V T177S F180Y | 106 |
| I137E S173Y G174S S175A F180Y | 108 |
| S144Q S173Y G174S S175A F180Y | 98 |
| Q70N S173Y G174S S175A F180Y | 105 |
| S173Y G174S S175A F180Y S274I | 95 |
| S173Y G174S S175A F180Y V286Q | 112 |
| V162R S173Y G174S S175A F180Y | 116 |
| I121V S173Y G174S S175A F180Y | 123 |
| L81V S173Y G174S S175A F180Y | 116 |
| A102T S173Y G174S S175A F180Y | 101 |
| S173P G174T S175A T177S F180Y | 111 |
| S171N S173Y G174S S175A F180Y | 103 |
| S173P G174K S175P N176G T177S F180Y | 107 |
| D155N G159S S173Y G174S S175A F180Y | 97 |
| V162R S173P G174T S175V T177S F180Y | 124 |
| I121V S173P G174T S175V T177S F180Y | 109 |
| L81V S173P G174T S175V T177S F180Y | 102 |
| I137E S173P G174T S175V T177S F180Y | 104 |
| S144Q S173P G174T S175V T177S F180Y | 95 |
| Q70N S173P G174T S175V T177S F180Y | 98 |
| S173P G174T S175V T177S F180Y S274I | 116 |
| S173P G174T S175V T177S F180Y V286Q | 98 |
| S171N S173P G174T S175V T177S F180Y | 101 |
| L81V I137E S173Y G174S S175A F180Y | 97 |
| I137E S173Y G174S S175A F180Y S274I | 109 |
| I137E S173Y G174S S175A F180Y T297P | 100 |
| I137E S173P G174T S175A T177S F180Y | 104 |
| S173P G174T S175V T177S F180Y T297P | 113 |
| T40L I137E S173Y G174S S175A F180Y | 96 |
| S173P G174K S175A N176G T177S F180Y | 112 |
| I137E S173Y G174S S175A F180Y V286Q | 98 |
| D155N G159S S173P G174T S175V T177S F180Y | 107 |
| V162R S173P G174K S175P N176G T177S F180Y | 113 |

TABLE 7d-continued

Wash performance of protease variants on a Blood, Milk, Ink stain, reference enzyme is TY-145 (SEQ ID NO: 3)

| Mutations | Wash performance relative to SEQ ID NO: 3, at 20° C. on C-05 |
|---|---|
| I121V S173P G174K S175P N176G T177S F180Y | 116 |
| L81V S173P G174K S175P N176G T177S F180Y | 114 |
| A102T S173P G174K S175P N176G T177S F180Y | 106 |
| S173P G174K S175P N176G T177S F180Y T241P | 94 |
| I137E S173P G174K S175P N176G T177S F180Y | 122 |
| S144Q S173P G174K S175P N176G T177S F180Y | 109 |
| S173P G174K S175P N176G T177S F180Y V286Q | 99 |
| T40D S173P G174K S175P N176G T177S F180Y | 105 |
| S171N S173P G174K S175P N176G T177S F180Y | 116 |
| L81V I137E S173P G174T S175V T177S F180Y | 100 |
| Q70N I137E S173P G174T S175V T177S F180Y | 113 |
| I137E S173P G174T S175V T177S F180Y V286Q | 109 |
| I137E S171N S173P G174T S175V T177S F180Y | 102 |
| I137E S173P G174K S175A N176G T177S F180Y | 119 |
| G132I S173P G174K S175P N176G T177S F180Y | 107 |
| S173P G174K S175P N176G T177S F180Y T297P | 109 |
| I137E S173P G174T S175V T177S F180Y S274I | 99 |
| D155N G159S S173P G174K S175P N176G T177S F180Y | 115 |
| S173P G174K S175P N176G T177S F180Y S274I | 106 |
| I121V I137E S173P G174K S175P N176G T177S F180Y | 153 |
| I137E S173P G174K S175P N176G T177S F180Y S274I | 100 |
| I137E S173P G174K S175P N176G T177S F180Y V286Q | 113 |
| I137E S173P G174K S175P N176G T177S F180Y T297P | 126 |
| I137E S171N S173P G174K S175P N176G T177S F180Y | 122 |

Example 4

The wash performance of exemplary detergents was determined by using the following standardized stains:

A: blood, milk, ink on cotton: product no. C-05 obtainable from CFT (Center for Testmaterials) B.V., Vlaardingen, Netherlands, B: groundnut oil, pigment, high milk on cotton: product no. C-10 obtainable from CFT (Center for Testmaterials) B.V., Vlaardingen, Netherlands, C: grass on cotton: product no. E164 obtainable from Eidgenössische Material- and Prüfanstalt (EMPA) Testmaterialien AG [Federal materials and testing agency, Testmaterials], St. Gallen, Switzerland.

A liquid washing agent with the following composition was used as base formulation (all values in weight percent): 0 to 0.5% xanthan gum, 0.2 to 0.4% antifoaming agent, 6 to 7% glycerol, 0.3 to 0.5% ethanol, 0 to 7% FAEOS (fatty alcohol ether sulfate), 10 to 28% nonionic surfactants, 0.5-1% boric acid, 1 to 2% sodium citrate (dihydrate), 2 to 4% soda, 0 to 16% coconut fatty acid, 0.5% HEDP (1-hydroxyethane-(1,1-diphosphonic acid)), 0 to 0.4% PVP (polyvinylpyrrolidone), 0 to 0.05% optical brighteners, 0 to 0.001% dye, remainder deionized water.

Based on this base formulation, various detergents according to embodiments herein were prepared by adding respective proteases as indicated in tables 8a & b. Reference is the protease that has the amino acid sequence described in FIG. 2 and SEQ ID NO: 3 of WO 03/055713, the reference protease already showing a good wash performance, especially in liquid detergents. The proteases were added in the same amounts based on total protein content (5 mg/l wash liquor).

The dosing ratio of the liquid washing agent was 4.7 grams per liter of washing liquor and the washing procedure was performed for 60 minutes at a temperature of 20° C. and 40° C., the water having a water hardness of from about 15.5 to about 16.5° (German degrees of hardness).

The whiteness, i.e. the brightening of the stains, was determined photometrically as an indication of wash performance. A Minolta CM508d spectrometer device was used, which was calibrated beforehand using a white standard provided with the unit.

The results obtained are the difference values between the remission units obtained with the detergent according to embodiments herein and the remission units obtained with the detergent containing the reference protease. A positive value therefore indicates an improved wash performance of the detergent of embodiments herein. It is evident from tables 8a (results at 40° C.) and 8b (results at 20° C.) that detergents according to embodiments herein show improved wash performance.

TABLE 8a

Wash performance of protease variants that have the same amino acid sequence as TY-145 (SEQ ID NO: 3) except for the substitutions as per the table below on a blood, milk, ink stain on cotton (A); reference is the protease that has the amino acid sequence described in FIG. 2 and SEQ ID NO: 3 of WO 03/055713.

| Protease variant | A |
|---|---|
| I137E + S137P | 2.9 |
| S173P + S175P + F180Y (variant 2) | 3.2 |
| I137E + S137P + G174T + S175V + T177S + F180Y | 3.5 |
| S137P + G174T + S175V + T177S + F180Y + S274I | 2.6 |
| S137P + G174T + S175V + T177S + F180Y + T297P | 3.6 |
| S173P + S175P + F180Y + V286Q | 2.5 |

TABLE 8b

Wash performance of protease variants on a blood, milk, ink stain on cotton (A), groundnut oil, pigment, high milk on cotton (B); grass on cotton (C); reference is the protease that has the amino acid sequence described in FIG. 2 and SEQ ID NO: 3 of WO 03/055713.

| Protease variant | A | B | C |
|---|---|---|---|
| I137E + S137P | 2.5 | 1.9 | 0.7 |
| S173P + S175P + F180Y (variant 2) | 1.6 | 0.8 | 0.9 |
| I137E + S137P + G174T + S175V + T177S + F180Y | 2.0 | 2.1 | 0.6 |
| S137P + G174T + S175V + T177S + F180Y + S274I | 1.5 | 2.0 | 1.6 |
| S137P + G174T + S175V + T177S + F180Y + T297P | 3.1 | 1.6 | 1.2 |
| S173P + S175P + F180Y + V286Q | 2.0 | 0.6 | 1.0 |

Example 5

The stability of variant 2 as defined in example 4 and a non-protease enzyme (Mannanase) was tested in the liquid detergent composition as described above in Example 4 and according to the following protocol:

1. Enzyme Preparation: The correct % of the enzyme preparation is added to the formulation and the formulation is then stored for 8 Weeks at 30° C.
2. Protease activity: The enzyme activity can be measured according to methods known in the art. Enzyme activity assays are well known to the person skilled in the art and are routinely used. Protease activity assays are for example disclosed in Tenside, volume 7 (1970), pages 125-132. The protease activity can further be determined using the Suc-AAPF-pNA activity assay which measures the release of para-nitroanilin (pNA) from the substrate suc-L-Ala-L-Ala-L-Pro-L-Phe-p-nitroanilide (suc-AAPF-pNA. The release of the pNA causes an increase in extinction at 410 nm, of which the curve over time is a measure of enzymatic activity (cf. Del Mar et al., 1979). The measurement is conducted at temperatures of 25° C., at pH 8.6 and a wavelength of 410 nm. The measuring period is 5 min. with a measuring interval of 20 s to 60 s. The protease activity may be expressed in PU (protease units).
3. Mannanase activity: After storage the remaining mannanase activity was measured as described in "Assay of endo-1,4-beta-Mannanase using Beat Annanase Tablets" (Fa. Megazyme). Enzyme samples were incubated in with Azurine-crosslinked cardo Galactomannan in 0.2 M Tris HCl pH 8.2. The reaction was followed spectroscopically at 590 nm.
4. Calculations: all activities are expressed as relative activities, either relative to the start value or relative to the normed activity of the control non-"diluted" granulate mix.

The stability of variant 2 was tested in the liquid detergent composition as described above in Example 4. To assess the effect of borate and 4-formylphenyl boronic acid (4-FPBA) on the stability of variant 2, these two components were added to the liquid detergent composition separately or in combination in varying concentrations as per table 9a below.

TABLE 9a

Stability of variant 2 in liquid detergent composition containing varying concentrations of Borate and 4-formylphenyl boronic acid (4-FPBA).

| | Protease variant stability | |
|---|---|---|
| | Without Borate | With 1% w/w Borate |
| 0.9% w/w variant 2 (2% (w/w) 4-FPBA) | 65% | 79% |
| 0.9% w/w variant 2 (0% (w/w) 4-FPBA) | 11% | 80% |
| 0.9% w/w variant 2 (1% (w/w) 4-FPBA) | 57% | 84% |

The stability of a non-protease enzyme in the liquid detergent preparation containing variant 2 was tested by adding 0.00001% of active Mannanase (Mannaway™ by Novozymes) to the composition.

TABLE 9b

Stability of Mannanase in a liquid detergent composition containing variant 2 and varying concentrations of Borate and 4-formylphenyl boronic acid (4-FPBA).

| | Mannanase stability | |
|---|---|---|
| | Without Borate | With 1% w/w Borate |
| 0.9% w/w variant 2 (2% (w/w) 4-FPBA) | 30% | 85% |
| 0.9% w/w variant 2 (0% (w/w) 4-FPBA) | 0% | 81% |
| 0.9% w/w variant 2 (1% (w/w) 4-FPBA) | 15% | 85% |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the subject matter in any way. Rather, the foregoing detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalent

The invention claimed is:

1. A detergent composition comprising a protease variant, the protease variant comprising a substitution of an amino acid in the loop corresponding to position 173 of SEQ ID NO: 3, wherein
   (a) the variant has a sequence identity to SEQ ID NO: 3 of at least 70% and less than 100%, and
   (b) the variant has protease activity, and
   (c) the amino acid at the position corresponding to position 173 of SEQ ID NO: 3 is Pro.

2. The detergent composition of claim 1, wherein the protease comprises substitutions at two positions corresponding to position 173 and any one of position 171, 175, 179, and 180.

3. The detergent composition of claim 2, wherein in the protease variant
   a) the amino acid at the position corresponding to position 171 of SEQ ID NO: 3 is selected from the group consisting of Trp, Lys, Glu, or
   b) the amino acid at the position corresponding to position 175 of SEQ ID NO: 3 is Ala, Val, Pro, or
   c) the amino acid at the position corresponding to position 179 of SEQ ID NO: 3 is selected from the group consisting of Cys, Val, Gln, Ser, Thr, Glu, His, Lys, Met, Asn.

4. The detergent composition of claim 2, wherein in the protease variant the amino acid at the position corresponding to position 180 of SEQ ID NO: 3 is Tyr.

5. The detergent composition of claim 1, wherein the protease variant comprises one or more substitutions selected from the group consisting of Y39D; T40{D,P}; Q7ON; T74M; L81{F,H,V}; A102T; I121{V,T}; G132{I,E}; I137{M; E}; S144{Q,R}; D155N; G159S; V162R; G174{S,T}; N176G; T177S; T241P; I247M; H256F; S274I; V286Q; T297P.

6. The detergent composition of claim 1, wherein the protease variant is selected from the variants that comprise any of the following substitutions compared to SEQ ID NO. 3:

S173P S274I
I137M S173P
S171N S173P
L81F S173P
L81H S173P
A102T S173P
S144Q S173P
I137E S173P
S173P S175P F180Y
S173P G174T S175V T177S F180Y
S173P G174K S175P N176G T177S F180Y

S173P T241P
V162R S173P G174T S175V T177S F180Y
I121V S173P G174T S175V T177S F180Y
L81V S173P G174T S175V T177S F180Y
A102T S173P G174T S175V T177S F180Y
S173P G174T S175V T177S F180Y T241P
I137E S173P G174T S175V T177S F180Y
S144Q S173P G174T S175V T177S F180Y
Q70N S173P G174T S175V T177S F180Y
D155N G159S S173P G174T S175V T177S F180Y
S173P G174T S175V T177S F180Y S274I
S173P G174T S175V T177S F180Y V286Q
T40D S173P G174T S175V T177S F180Y
S171N S173P G174T S175V T177S F180Y
V162R S173P G174K S175P N176G T177S F180Y
I121V S173P G174K S175P N176G T177S F180Y
L81V S173P G174K S175P N176G T177S F180Y
A102T S173P G174K S175P N176G T177S F180Y
S173P G174K S175P N176G T177S F180Y T241P
I137E S173P G174K S175P N176G T177S F180Y
S144Q S173P G174K S175P N176G T177S F180Y
Q70N S173P G174K S175P N176G T177S F180Y
D155N G159S S173P G174K S175P N176G T177S F180Y
S173P G174K S175P N176G T177S F180Y S274I
S173P G174K S175P N176G T177S F180Y V286Q
T40D S173P G174K S175P N176G T177S F180Y
S171N S173P G174K S175P N176G T177S F180Y
I121V I137E S173P G174T S175V T177S F180Y
L81V I137E S173P G174T S175V T177S F180Y
I137E S173P G174T S175V T177S F180Y T241P
Q70N I137E S173P G174T S175V T177S F180Y
I137E S173P G174T S175V T177S F180Y V286Q
I137E S173P G174T S175V T177S F180Y T297P
I137E S171N S173P G174T S175V T177S F180Y
I137E S173P G174T S175A T177S F180Y
I121V I137E S173P G174K S175P N176G T177S F180Y
Q70N I137E S173P G174K S175P N176G T177S F180Y
I137E S173P G174K S175P N176G T177S F180Y S274I
I137E S173P G174K S175P N176G T177S F180Y V286Q
I137E S173P G174K S175P N176G T177S F180Y T297P
I137E S171N S173P G174K S175P N176G T177S F180Y
I137E S173P G174K S175A N176G T177S F180Y
G1321 S173P G174T S175V T177S F180Y
S173P G174T S175V T177S F180Y T297P
S173P G174T S175A T177S F180Y
S173P S175A
I137E S173P S175V T177S F180Y
I137E S173P S175P N176G T177S F180Y
S173P G174K S175A N176G T177S F180Y
I137E S173P G174T S175V T177S F180Y S274I
T74M I137E S173P
T79I I137E S173P
L81G S173P
L34I I137E S173P
Y39D I137E S173P
T40P I137E S173P
I137E S173P I247M
I137E S173P H256F
I137E S144Q S173P G174T S175V T177S F180Y
I137E S144Q S173P G174K S175P N176G T177S F180Y
S173P G174T V175P T177S F180Y
I137E S173P G174T V175P T177S F180Y
I137E S173P G174T V175P T177S F180Y T297P
V162R S171N S173P G174K S175P N176G T177S F180Y
I137E S171N S173P G174K S175P N176G T177S F180Y T241P
I137E S171N S173P G174K S175P N176G T177S F180Y T297P
I137E S173P S175P F180Y
V162R S173P S175P F180Y
S173P S175P F180Y S274I
S173P S175P F180Y T241P
S173P S175P F180Y T297P
S173P S175P F180Y V286Q.

7. The detergent composition of claim 6, wherein the protease variant has an improved detergent stability compared to the protease with SEQ ID NO: 3.

8. The detergent composition of claim 7, the composition further comprising a borate and/or 4-formylphenyl boronic acid.

9. The detergent composition of claim 8, wherein the protease variant is selected from the group consisting of:

a) a polypeptide having at least 70% sequence identity to the mature polypeptide of SEQ ID NO: 2;

b) a polypeptide encoded by a polynucleotide that hybridizes under medium, or high stringency conditions with (i) the mature polypeptide coding sequence of SEQ ID NO: 1, (ii) a sequence encoding the mature polypeptide of SEQ ID NO: 2, or (iii) the full-length complement of (i) or (ii);

c) a polypeptide encoded by a polynucleotide having at least 60% identity to the mature polypeptide coding sequence of SEQ ID NO: 1, or a sequence encoding the mature polypeptide of SEQ ID NO: 2; and d) a fragment of the mature polypeptide of SEQ ID NO: 2, which has protease activity.

10. The detergent composition of claim 9, wherein (a) the protease variant has at least 75%, but less than 100%, sequence identity to the mature polypeptide of SEQ ID NO: 3; and (b) in the protease the total number of alterations is from 1 to 20.

11. The detergent composition of claim 9, wherein (a) the protease variant has at least 85%, but less than 100%, sequence identity to the mature polypeptide of SEQ ID NO: 3; and (b) in the protease the total number of alterations is from 1 to 10.

12. The detergent composition of claim 9, wherein (a) the protease variant has at least 90%, but less than 100%, sequence identity to the mature polypeptide of SEQ ID NO: 3; and (b) in the protease the total number of alterations is from 1 to 5.

13. The detergent composition of claim 9, wherein (a) the protease variant has at least 95%, but less than 100%, sequence identity to the mature polypeptide of SEQ ID NO: 3; and (b) in the protease the total number of alterations is from 1 to 5.

14. The detergent composition of claim 9, wherein (a) the protease variant has at least 99%, but less than 100%, sequence identity to the mature polypeptide of SEQ ID NO: 3; and (b) in the protease the total number of alterations is from 1 to 5.

15. The detergent composition of claim 9, wherein (a) the composition is in form of a bar, a homogenous tablet, a tablet having two or more layers, a pouch having one or more compartments, a regular or compact powder, a granule, a paste, a gel, or a regular, compact or concentrated liquid; and/or
(b) the composition further comprises one or more additional enzymes selected from protease, lipase, cutinase, amylase, carbohydrase, cellulase, pectinase, mannanase, arabinase, galactanase, xylanase, oxidase, laccase, and peroxidase.

16. The detergent composition of claim 9, wherein the composition is a laundry detergent composition.

17. The detergent composition of claim 9, wherein the composition is a dishwashing composition.

18. A method for using a detergent composition in a cleaning process, wherein the detergent composition comprises a protease variant comprising a substitution of an amino acid in the loop corresponding to position 173 of SEQ ID NO: 3, wherein
   (a) the variant has a sequence identity to SEQ ID NO: 3 of at least 70% and less than 100%,
   (b) the variant has protease activity, and
   (c) the amino acid at the position corresponding to position 173 of SEQ ID NO: 3 is Pro; and
wherein the method comprises treating fabrics with a washing solution containing the detergent composition.

19. The method of claim 18 wherein the cleaning process is a machine washing process.

20. The method of claim 18 wherein the cleaning process is a manual washing process.

* * * * *